United States Patent [19]

Peoples et al.

[11] Patent Number: 5,245,023
[45] Date of Patent: Sep. 14, 1993

[54] METHOD FOR PRODUCING NOVEL POLYESTER BIOPOLYMERS

[75] Inventors: Oliver P. Peoples, Arlington; Anthony J. Sinskey, Boston, both of Mass.

[73] Assignee: Massachusetts Institute of Technology, Cambridge, Mass.

[21] Appl. No.: 700,109

[22] Filed: May 8, 1991

Related U.S. Application Data

[63] Continuation of Ser. No. 378,155, Jul. 10, 1989, abandoned, which is a continuation-in-part of Ser. No. 67,695, Jun. 29, 1987, abandoned.

[51] Int. Cl.$^5$ .................. C12N 15/60; C12N 9/88; C12P 7/62
[52] U.S. Cl. .................. 536/23.2; 435/232; 435/135; 435/190; 435/191; 435/193
[58] Field of Search ............. 435/232, 135, 190, 191, 435/193; 528/361; 536/27

[56] References Cited

U.S. PATENT DOCUMENTS 4,477,654 10/1984 Holmes et al. .................. 528/361

OTHER PUBLICATIONS

Senior and Dawes, *Biochem. J.*, 134, 225–238 (1973).
Oeding and Schlegel, *Biochem. J.*, 134, 239–248 (1973).
Bernt and Schlegel, *Arch. Microbiol.*, 103, 21–30 (1975).
Nishimura et al., *Arch Microbiol.*, 116, 21–27 (1978).
Saito et al., *Arch. Microbiol.*, 114, 211–217 (1977).
Fukui, et al. *Biochim Biophys. Acta* 917, 365–371 (1987).
Griebel and Merrick, *J. Bacteriol.*, 108, 782–789 (1971).
Fukui et al., *Arch Microbiol.*, 110, 149–156 (1976).
Steven C. Slater, et al., *J. Bacteriol.* 107(10), 4431–4436 (Oct. 1988).
Peter Schubert, et al., *J. Bacteriol.* 170 (12), 5837–5847 (Dec. 1988).
Tomita, K., et al. (1982) Symposium in Honor of Dr. H. A. Lardy, Jun. 9–11, 1982, pp. 1–14.

*Primary Examiner*—Charles L. Patterson, Jr.
*Attorney, Agent, or Firm*—Kilpatrick & Cody

[57] ABSTRACT

A method for controlling and modifying biopolymer synthesis by manipulation of the genetics and enzymology of synthesis of polyhydroxybutyrate (PHB) and polyhydroxyalkanoate (PHA) polyesters at the molecular level in procaryotic and eukaryotic cells, especially plants. Examples demonstrate the isolation, characterization, and expression of the genes involved in the production of PHB and PHA polymers. Genes encoding the enzymes in the PHB and PHA synthetic pathway (beta-ketothiolase, acetoacetyl-CoA reductase and PHB polymerase or PHA polymerase) from *Zoogloea ramigera* strain I-16-M, *Alcaligenes eutrophus*, *Nocardia salmonicolur*, and *Psuedomonas olevarans* were identified or isolated and expressed in a non-PHB producing organism, *E. coli*. Specific modifications to the polymers include variation in the chain length of the polymers and incorporation of different monomers into the polymers to produce co-polymers with different physical properties.

2 Claims, 17 Drawing Sheets

FIGURE 1

```
ACAATCGAAT TGTGCGATGC GGGGAGGGAT GCTGCGCAAC ATGGATTTTC ATGCTGCGGG GCCCCCCGGA TGAAATTTTA GGGCCGCCGG ATATCCCTGACTCTCCT
-210        -190                  -170        -150                  -130        -110        -90         -70         -50          -30

EcoRI
GAATTCCTCA TCCCCGTGTT CCTCTTTTCT TTTTTGAGCC TTGGGAGTAT CCGCAAAACGGCTTCCTG
      -170                    -150                  -130               -110

-10
TCTCCGCTTT GCCAGTTTTG ATTTCGGGAC AACCCGCCGG CTCGCGCCCG TCGTGCCCCG GACCCCGGTC CAAGGCCCGC CGGAAGGCTG CCAGAACTGAAGCACAT
           RNA →                        30                    50                    70                    90

ATG AGC ACC CCG TCC ATC GTC ATC GCC AGC GCC CGC ACC GCG GTC GGT TCC TTC AAC GGC GCT TTC GCC AAC ACG CCC GCC GAA CTC
Met Ser Thr Pro Ser Ile Val Ile Ala Ser Ala Arg Thr Ala Val Gly Ser Phe Asn Gly Ala Phe Ala Asn Thr Pro Ala Glu Leu
    10                      110                     130                     150                     170

GGG GCG ACC GTG ATT TCG GCG GTT CTC GAG CGC CGG GGC GAG GTG AAC GAG GTG ATT CTC GGC GTG CCG
Gly Ala Thr Val Ile Ser Ala Val Leu Glu Arg Arg Gly Ala Ala Gly Val Ala Asn Glu Val Ile Leu Gly Val Pro Ala
    190                     210                     230                     250                     270

GGC GAA GGC CAG AAC CCG GCC CGG CAG GCG GTG CCG CAG GAG GCG ACC GCC TGG GGC ATG AAC CAG TGC GGC
Gly Glu Gly Gln Asn Pro Ala Arg Gln Ala Val Pro Gln Glu Ala Thr Ala Trp Gly Met Asn Gln Cys Gly
    290                     310                     330                     350

TCG CGG CGC GTC GCG CTC GGC ATG CAG CAG ATC GCC GAT GCG AGC ATC GTC GCC GGC ATG GAA ATG TCC
Ser Gly Leu Arg Ala Val Ala Leu Gly Met Gln Gln Ile Ala Asp Ala Ser Ile Val Ala Gly Met Glu Met Ser
    370                     390                     410                     430                     450

ATG GCC CCG CAT TGC GCG CAT CTG GCC CTG GCC GGC GTG AAG ATG GGC GAT TTC AAG ATG ATC GAC AAG GAC GGC CTG GAC GCC
Met Ala Pro His Cys Ala His Leu Ala Leu Ala Gly Val Lys Met Gly Asp Phe Lys Met Ile Asp Lys Asp Gly Leu Asp Ala
    470                     490                     510                     530

TTC TAC GGC TAC CAC ATG GGC AAT GTC GCC AAG CAG TGG CAG CTT TCC CGC GAC GAG CAG GAC GCC TTC GTC GCC
Phe Tyr Gly Tyr His Met Gly Thr Ala Glu Asn Val Ala Lys Gln Trp Gln Leu Ser Arg Asp Glu Gln Asp Ala Phe Val Ala
```

```
TCG CAG AAC AAG GCC GAG GCC CAG AAG GAC GGC CGC TTC AAG GGC GC GAC ATC
Ser Gln Asn Lys Ala Glu Ala Gln Lys Asp Gly Arg Phe Lys Gly Arg ly Asp Ile
                        650                     670                  690           7

ACG GTC GAT GCC GAC GAA TAT CGC CAC ACG GCC GGC CAC CTC GAT TCC ATG GCG GAG ATC GTT CCC TTC ATC GTC AAG GGC CGC GC GAC ATC
Thr Val Asp Ala Asp Glu Tyr Ile Arg His Gly Ala Thr Leu Asp Ser Met Ala Lys Pro Ala Phe Asp Lys ly Thr Val
                        730                     750                  770                   790                       810

ACG GCC GGC AAC GCC TCC GGC CTC AAT GAC GGC GCG GCC GCG CTG ATG AGC GAA GCG TCG CGC CGC TC CAG CCG
Thr Ala Gly Asn Ala Ser Gly Leu Asn Asp Gly Ala Ala Ala Leu Leu Met Ser Glu Ala Ser Arg Arg le Gln Pro
                        830                     850                  870                                   8'

CTC GGC CGC ATC GTT TCC TGG GCG ACG GTC GTC GGC GTC ATG CCC AGG GGC ACC CCG ATC TCC CGC CGC CTC GAG
Leu Gly Arg Ile Val Ser Trp Ala Thr Val Gly Val Met Gly Thr Gly Pro Ile Pro Ala Ser Arg la Leu Glu
                        910                     930                  950                   970                       990

CGC GCC GGC TGG AAG ATC GGC GAT CTC GAC CTC GTG GAA GCC AAC GAA GCC TTC GCG CAG GCC GGC GTC TGC GGC GTC AAC AC CTC GGC
Arg Ala Gly Trp Lys Ile Gly Asp Leu Asp Leu Val Glu Ala Asn Glu Ala Phe Ala Gln Ala Gly Val Cys Ala Val Asn bp Leu Gly
                        1010                    1030                 1050                                  10

TGG GAT CCG TCC ATC GTC AAC GGT GCC AAC GTC AAT GGT GCC ATC GGC CAC CCG ATC GGC ATC GGC TCC GGC GCC ATC GGC CGC AC ACG CTC
Trp Asp Pro Ser Ile Val Asn Gly Ala Asn Val Asn Gly Ala Ile Gly His Pro Ile Gly Ala Ser Gly Ala Arg Ile bn Thr Leu
                        1090                    1110                 1130                  1150                      1170

CTC TTC GAG ATG AAG CGT CGC GGC CGC CGC AAG GGT CTC GCC ACG CTC TGC ATC GGC CGC ATG GGC GTG GCG GGC ATG TC GAG AGC
Leu Phe Glu Met Lys Arg Arg Gly Arg Arg Lys Gly Leu Ala Thr Leu Cys Ile Gly Arg Met Gly Val Ala Gly Met le Glu Ser
                        1190                    1210                 1230

CTT TAG GCG TCA GCT TAT CCA AAA CTT TGC CAT GAC CTG CCG CCG AGG GCG ACA GGT CGA C
Leu End                                                                    Sal1
```

```
    Sal
  1 GTCGACTCAAAAATCAGTCTAGGGAGTGAGGAGGTAGCATTGTAACGGGGGATCGGGGCATCGGGCCAGCCTCGATT     96
                         MetSerArgValAlaLeuValThrGlyGlySerArgGlyIleGlyAlaAlaSerIle

97 GCGCTGAAGGCGGGGGATACAAGGTGGCTGCCAGCTATGCCGGCAATGACGATGCCCAAGCCCTTCAAGGCGGAAACGGGCATGTCTAC    192
    AlaLeuLysAlaGlyAlaAlaGlyTyrLysValAlaAlaSerTyrAlaGlyAsnAspAspAlaAlaLysProPheLysAlaGluThrGlyIleValTyr

193 AAGTGGGACGTGTCGAGCTACGAGGCCTGCGTCGAGGGATCCCAAGGTGGAGGCCGATTGACGTTCTCGTCAAGCGGGC    288
    LysTrpAspValSerSerTyrGluAlaCysValGlyIleAlaLysValGlyIleAlaAspLeuValProIleAspValAlaAsnAlaGly

289 ATCACCAAGGACGCGATGTTCCACAAGATGACGCCCGACCAGTGGAATGCGGTCATCAACAACCTCACGGGTCTCTTCAACATCATCCG    384
    IleThrLysAspAlaMetPheHisLysMetThrProAspGlnTrpAsnAlaValIleAsnThrLeuThrGlyLeuPheAsnMetHisPro

385 GTCTGTCCGGCATGCGCCGACCGCAGCTTCGGGCGATCAACATCTCCTCGATCAACATCAACGGGCCAGAAGGCCAGATGGTCAGGCCATTCC    480
    ValTrpSerGlyMetArgAspArgSerPheGlyArgIleValAsnIleSerSerIleAsnGlyGlnLysGlyGlnMetGlyGlnAlaTyrSer

481 GCCGCCAAGGCCGGCGACCTCGGCTTCACCAAGGCGCTGGCAGGAAGGCGCTCAAGGGCCATCACGTTCAAGCGCCATCTGCCCATATC    576
    AlaAlaLysAlaGlyAspLeuGlyPheThrLysAlaLeuAlaGlyGlyArgGluGlyAlaLeuLysGlyIleThrValAsnAlaIleCysProTyrIle

577 GGTACGGAAATGGTGCGCGCCATTCCGGAAAAGGTGCTGAAGCAGAGCGGGATCATCCCGGAGATCATCCCGAGATCCCGGCCTCGGGCGAGCCGAGATC    672
    GlyThrGluMetValArgAlaIleProGluLysValLeuAsnGluArgIleIleProGlnIleProValGlyArgLeuGlyGluProGluIle

673 GCCCGCATCGTCGTCTTCCTCGCCTCGACGAGGCCGGCTTCATCACCGGCTCGACCATCTCGGGCGAACGGCCAGTTCTTCGTCGTTGTACCGG    768
    AlaArgIleValValPheLeuAlaSerAspGluAlaGlyPheIleThrGlySerThrIleSerAlaAsnGlyGlyGlnPheVal'
```

```
 769 CCACACGAAACGGAACGGGGCGCCTTCGGGCGGCCGTTTTCATGTGGTATGTGGTCGAAAGGAGACCCCGATGAAACAGGAAAAGCTGAGG   864
 865 CGGCGATTGCCGAGGCGCTGGCATCCCTCGAAGGATGATTCGCTCGGCTGACGCGCCATCGAGAAGCGCTACACGTTCAAGACCGCG       960
                                                                                       Sal
 961 AGGGCGTTCGGCTTCATGACCGAGGGCGCTGGGGCGGAGAAATTCAACCACCATCCCGAATGGTTCAACGTCTACAATCGGTCGCGGC     1056
1057 TGACCAACCACGATGCGGGGCGCTGACCGAGCTTCAAGCTGGCGGCGATGGAGAAGGCGGCCTTTCGCACGAAGAAAGCG             1152
1153 GCGTGAACGCATTCCCATATGATCAGCGCCGGACTGTTCCGGGCGCTGCCACCCGAGGAGCCTTGAATGGACGATGTGAAGATCGGATTCT   1248
1249 GCTGCCCGGCGACAAGGACGAGGAGCAGCCCGTCAGGAAAGCCCGTGAGGCGGTTCTGGCCGCTCTCAAGCCCGATGGGCCACCCTT       1344
                                                 Sma
1345 CGCCCCGGCGATCTCGTCGGTCTACTATTGCGCGCTCGATCCCCACACGCCCGGCGCGGGCCATCCTGCTGCCGGGGCCTCGCTTTGT     1440
1441 GCTGCCGCTCGACGGCATACCGGATTTCTTCGCCTCGTCGGCTTTTCGACGACGTTGCCGTGCTGACGCGGCCCTTCGCGGCGATGGCCA   1536
1537 TGTTCGCGACGACCATTACGGCCCGCCGACCGGGGCCTTGCCGGACGAGCCGACATGCAACCCTTCGGTTGAGCCGGGCCGGTC         1632
1633 AAATTCTTGCCCTATTCCTGTGCCATTAGGCATCTCACCAAATGGGACTGGGCACGCCCGCTTTCACGAACTGCG                   1728
1729 GCGGACTTCGACACGGTTTCGTCCCCGTGCCGGGGGAAGACCTCGGCGGTTTGGTAACCTGAATTAAAAATA                     1824
1825 AATCAAATCGTCATCAAGCATGCCGACACCGGCGAATCACTGCCAAGACAACCGGCAGGAAGTTC                           1920
1921 GTAAGAAAGCTCGCAACCGGACTCGCCCTCGTCCTTGCCAGGCGTTGCCTCGGGCAAAGCCGACGGCATTCAGCAGTTCCCTGG         2016
2017 GGGCCCTATTCCTATCAGGGCGAATGCCGCAAGCTCTGCTGTCCGTGCCGAAGGAAAAGACGCCGGGCCCGGG  2094
                                                                          Sma
```

```
        10                  30                  50                  70                  90
Pst      .         .         .         .         .         .         .         .         .
CTGCAGGTTCCCTCCCGTTCCATTGAAAGGACTACACAATGACTGACGTTGTCATCGTTATCCCGCCACCGGCCGTTGGCGGC
                                    MetThrAspValValIleValSerAlaAlaArgThrAlaValGPheGlyGly 110                 130                 150                 170                 190
         .         .         .         .         .         .         .         .         .
TCGCTGGCCAAGATCCGGCACCGGAACTGGTGCCGTGTCATCAAGGCCGCTGAGCGCCGGCGTCAAGCCGGAGCAGGAAGTC
SerLeuAlaLysIleProAlaProGluLeuGlyAlaValValIleLysAlaAlaLeuGluArgArgArgValLysProGluGluSerGluVal 210                 230                 250                 270
         .         .         .         .         .         .         .
ATCATGGGCCAGGTGCTGACCGTTCGGGCCAGAACCCCGCACGCCAGGCCCGATCAAGGCCCGCTGCCGATGCTCCATGACC
IleMetGlyGlnValLeuThrAlaGlySerGlyGlnAlaArgGlnAlaAlaIleLysAlaGlyLeuProAlaMetValMetThr 290                 310                 330                 350                 370
         .         .         .         .         .         .         .         .         .
ATCAACAAGGTGTGCGGTCGGGCTGAAGGCCGTGATGCTGGCCGCCAAGGCCGATCATGGGGCGACGCCGAGATCGTGGTGGCCCAG
IleAsnLysValCysGlySerGlyLeuLysAlaValMetLeuAlaAlaAsnAlaIleMetAlaGlyAspAlaGluIleValGlyGlyGln 390                 410                 430                 450
         .         .         .         .         .         .         .
GAAAACATGAGCGCCCCGCACGTGCTGCCGGGCTCGCGCGATGGTTCCGCATGGGCGATGCCAAGCTGTCGACACCAGTCGACGGC
GluAsnMetSerAlaAlaProHisValLeuProGlySerArgAspGlyPheArgMetGlyAspAlaLysLeuAlaAspThrMetAlaAspGly 490                 510                 530                 550                 570
         .         .         .         .         .         .         .         .         .
CTGTGGGACGTGTACAACCAGTACCACATGGGCATCACCCGCGAGAACGTGGCCAAGGAATACGGCATCACACGCGAGGCCGAGTTCGCC
LeuTrpAspValTyrAsnGlnTyrHisMetGlyIleThrArgGluAsnValAlaLysGluTyrGlyIleThrArgGluAlaGluPheAla
```

```
                590            610            630            650            670
GTCGGCTCGCAGAACAAGGCCGAAGGCCGAGAAGGCCCAAGTTTGACGAAGAGATCTCCCGTGCTGATCCCGACGGCGACCCG
ValGlySerGlnAsnLysAlaGluAlaAlaAlaGlyLysAlaGlyLysPheAspGluIleProValLeuIleProGlnArgGlyAspPro
                690            710            730            750
GTGGCCTTCAAGACCGACGAGTTCGTGCGCCAGGCGCCCACGCTGGACAGCATGTCCGGCCTTCAAGCCCGCCTTCGACAAGCCCGGTGACC
ValAlaPheLysThrAspGluPheValArgGlnGlyAlaThrLeuAspSerMetSerGlyLeuLysProAlaPheAspLysAlaThrValThr
  770            790            810            830            850
GCGGCCAACGCCTCGGGCCTGAACGACGGCGTGTGGTGTGATGTCGGTGGGGGCCAAGGCCAAGGAACTGGGCCTGACTGGCCACG
AlaAlaAsnAlaSerGlyLeuAsnAspGlyAlaValValValMetSerAlaAlaAlaLysGluLeuGlyLeuGlyLeuThrLeuAlaThr
                870            890            910            930    Ava.
ATCAAGAGCTATGCCAACGCCCGTCTGCATCCCAAGCGATGGCCATGGCCCTCCAAGCGCCCCTGTGCGCAGTGGACC
IleLysSerTyrAlaAsnAlaGlyValAspProLysValMetGlyValMetGlyProAlaSerLysArgAlaSerArgGluTrpThr
  970  Ava.          990           1010           1030          150
CCGCAAGACCTGACCTGATGGAGATCAACGAGCCTTTGCCGCCGTGCCAGGCGTGCACCAGCAGATGGCTGGGACACCAGGTCAAT
ProGlnAspLeuAspLeuMetGluIleAsnGluAlaPheAlaAlaGlnAlaLeuAlaValHisGlnMetGlyTrpAspThrLysValAsn
                1070           1090           1110          1130          1150
GTGAACGGCGGCGCCATCGCGGCCATCGGCGGGCTCGGGCCCTATCCGCGTATCCTCGTGACCCTGCTGCACGAGATGAACGTGACGCG
ValAsnGlyGlyAlaIleAlaAlaIleGlyHisProIleGlyAlaSerGlyCysArgIleLeuValThrLeuLeuHisGluMetLysArgAspAla
```

```
         1170                1190                1210                1230
AAGAAGGGCCTGGCCTCGCTGTGCATCGGCGGCGGCATGGGCGTGGCGCTGGCAGTCGAGCGCAAATAAGGAAGGGGTTTTCCGGGCGCGCG
LysLysGlyLeuAlaSerLeuCysIleGlyGlyGlyMetGlyValAlaLeuAlaValGluArgLys *

1260                1280                1300                1320             1340
     Ava                                    Dde
GTTGGCGCGGACCCGGCGACGATAACGAAGCCAATCAAGGAGTGGACATGACTCAGCGCATTGCGTATGTGACCGGCGGCATGGTATCGGA
                                                MetThrGlnArgIleAlaTyrValThrGlyGlyMetGlyIleGly 1360                1380                1400                1420
ACCGCCATTTGCCAGCGGCTGGCCAAGGATGGCTTTCGTGTGGTGGCCGGTTGCGGCCCCAACTCGCCGCGCCGCGAAAAGTGGCGCAGCAG
ThrAlaIleCysGlnArgLeuAlaLysAspGlyPheArgValValAlaGlyCysGlyProAsnSerProArgArgGluLysTrpLuGlnGln 1440             1460                1480                1500                1520
AAGGCCCTGGGCTTCGATTTCATTGCCTCGGAAGGCAATGTGGCTGACTGGGACTCGACCAAGACCGCATTCGACAAGGTCAAGTLGGTCGGC
LysAlaLeuGlyPheAspPheIleAlaSerGluGlyAsnValAlaAspTrpAspSerThrLysThrAlaPheAspLysValLysSuValGly 1540               1560                1580                1600                1620
GAGGTTGATGTGCTGATCAACAACGCCGGTATCACCCGCGACGTGGTGTTCCGCAAGATGACCCGCGCCGACTGGGATGCGGTGACACCAAC
GluValAspValLeuIleAsnAsnAlaGlyIleThrArgAspValValPheArgLysMetThrArgAlaAspTrpAspAlaValIspThrAsn
    1640                1660                1680                1700               1

CTGACCTCGCTGTTCAACGTCACCAAGCAGGTGATCGACGGCATGGCCGACCGTGGCTGGGGCCGCATCGTCAACATCTCGTCGGCGGGCAG
LeuThrSerLeuPheAsnValThrLysGlnValIleAspGlyMetAlaAspArgGlyTrpGlyArgIleValAsnIleSerSerVnGlyGln
        1740                1760                1780                1800            1820

AAGGGCCAGTTCGGCCAGACCAACTACTCCACCGCCAAGGCCGGCCTGCATGGCTTCACCATGGCACTGGCGCAGGAAGTGGCGAGGGCGTG
LysGlyGlnPheGlyGlnThrAsnTyrSerThrAlaLysAlaGlyLeuHisGlyPheThrMetAlaLeuAlaGlnGluValAlaTysGlyVal 1840                1860                1880                1900
ACCGTCAACACGGTCTCTCCGGGCTATATCGCCACCGACATGGTCAAGGCGATCCGCCAGGACGTGCTCGACAAGATCGTCGCGATCCCGGTC
ThrValAsnThrValSerProGlyTyrIleAlaThrAspMetValLysAlaIleArgGlnAspValLeuAspLysIleValAla1eProVal
```

```
1920              194                1960              1980              )00
 .                 .                  .                 .                 .
AAGCGCCTGGGCCTGCCGGA:CCTCGATCTGCCGCTCTGGGAGGAGTCCGGTTTC:CCGACTTCTCGCTCAAC
LysArgLeuGlyLeuProGlIlaSerIleCysAlaTrpErGluGluSerGlyPheAlaAspPheSerLeuAsn
              2020              2060              2080              2100
               .                 .                 .                 .
GGGGGCCTGCATATGGGCTGGGCCTGGTCAACCAGTCGCGCTGGGCCCCGCGTLAGCCAGCGGGGCGACA
GlyGlyLeuHisMetGly *
            2120      0                         2180              2200
             .                                   .                 .
AGGGCGGGGCGTTCGTTTGTTTGTTTCGGGGCCGTCAAAATCGTTCTCGCCGCTCGCTTTTTGCGCCAAT
         2220              2240                           ·       2300
          .                 .                                      .
TCACCGGGTTTCCTTAAGCTTTTCTTAGTGCCTTGTGAATCAGGGGCCAGGCGGCCCATGTTCGTGCAGCGC
          2320       P
           .
GGCCCTCGCGGGGGCGAGCT(
```

*FIG CONT.*

```
       Sma
   1   CCCGGGCAAGTACCTTGCCGACATCTATGCGGCGCTGGCCGCGCCACGGCCTGTACGGAGGTCTACGGCGGCCTG        90
  91   CACCGTGGCGACGCCGGTCGCTTCTACTCCTATGGCGCCGATGGCGTGACCGGCCAGCCTGGTCTGGCTGGCGAGC       180
 181   CCGCCGCTGCCTCACTCGTCCTTGCCCCCTGGCCGGCCGCTCGGCTTGCTGGCGGGCCGGGCCGGGCGTGCCGATG       270
 271   TAGAGCACCACGGCCATGCCATACATCAGGAAGGTGCAACGCCTGCCACCACGTTGTCTCGGTGATCGGCCATAGCG       360
 361   CCACGTAGAGCCAGCCAATGGCCACGATGTACATCAAAAATTCATCTCGCCTATGCTCTCGGGGCCTCGGCAGATGCGATGCA   450
 451   TACCGTCCGGTAGGTCGGGAAGCGTGCAGTGCCGAGGCGGATTCCCGCCATTGACACGGCGTGCGTTGCAAGGCAACAATGGAAATG  540
 541   TCTCGGAATCGCTGACGATTCCCAGGTTTCTCCCGGCAGCATAGCGTCTCCATGCGAGAATGTCGGCTTGCCGGGAAGG    630
 631   GGAGCCGCTATCGGAATGACGCAAGCCACGGCCAGCAGTGTCGGTCGAGGGGCTTCCAGGCAGATGCCAGAC         720
 721   CCTCCCGGCTTTGGGGGAGGCGGCAAGCCGGTCCATTCGGATAGCATCTCCCCATGCAAAGTCCCGGCCAGGGCAATGCCCGGCGGTT    810
 811   CGAATAGTGACGGCAGAGAGACAATCAAATCATGGCACCGGCCAAGCGCGGCCAGCTTCCACGCAGGAAGGCAAGTCCCAATCAA      900
                                        M  A  T  G  K  G  A  A  A  S  T  Q  E  G  K  S  Q  F  K
 901   GGTCAGCGCCCGGGCCATTCGATCCAGCCACATGGCTGAATGGTCCGCCAGTGGCACTGAAGGCAACGGCCACGGHCGTC          990
         V  T  P  G  P  F  F  D  P  A  T  W  L  E  W  S  R  Q  W  Q  G  T  E  G  N  G  H  A  I  S
 991   CGGCATTCCGGGCCTGGATCGCTGGAGGCGTCAAGATCGCCCCGGCCAGCTGGGTGATATCCAGCAGGCTACATGAAGTCTC       1080
         G  I  P  G  L  D  A  L  A  G  V  K  I  A  P  A  Q  L  G  D  I  Q  Q  R  Y  M  K  F  S
1081   AGCGCTGTGCCAGGCCATGGCCGAGGCAAGGCCACCGGTCCGGCTGCACGACCGGCGCTTCGCCGGCGACGGCATGGCCAA         1170
         A  L  W  Q  A  M  A  E  G  K  A  E  A  T  G  P  L  H  D  R  R  F  A  G  D  A  W  :  N
1171   CCTCCCATATCGCTTCGCGCCGGTTCTACCTGCTCAATGCGCGCCTGACCGAGCTGGCCGATGCCGTCGAGGCCGATAGAC       1260
         L  P  Y  R  F  A  A  A  F  Y  L  L  N  A  R  A  L  T  E  L  A  D  A  V  E  A  D  K  T
```

*FIGURE 4*

```
1261  CGGCCAGCGCATCCGCTTCGCGATCTCGCAATGGTCGATGTCGCCCGCCAACTTCCTTGCCACCAATCCCGAGGCGCCT    1350
      R  Q  R  I  R  F  A  I  S  Q  W  V  D  A  M  S  P  A  N  F  L  A  T  N  P  E  A  R  L

1351  GCTGATCGAGTCGGGCGGCGCGAATGCCTGCGCCGTGCGCAACATGATGAAGACCTGACACGGGCAAGATCTCGCAAGACGA    1440
      L  I  E  S  G  G  E  S  L  R  A  G  V  R  N  M  H  E  D  L  T  R  G  K  I  S  Q  )  E

1441  GAGCGGCGTTGAGGTCGGCCCGCAATGTCGCGGTCGACCGTGTCTTCGAGAACGAGTACTTCCAGGTGTTGCAGAGCC    1530
      S  A  F  E  V  G  R  N  V  A  V  T  E  G  A  V  V  F  E  N  E  Y  F  Q  L  L  Q  (  P

1531  GCTGACCGACAAGGTGCACGGCGCGCCCGCTGATGGTGCCGCCCGTCATCAACAAGTACTACATCCTGGACCTGCAGCCGAGCTC    1620
      L  T  D  K  V  H  A  R  P  L  L  M  V  P  P  C  I  N  K  Y  Y  I  L  D  L  Q  P  ;  S

1621  GCTGGTGCGCCATGTGGTGGAGCAGGGACATACGGTGTTTCTGGTGTCGTGGCGCAATCCGGACGCCAGCATGGCCCAGGTGGGA    1710
      L  V  R  H  V  V  E  Q  G  H  T  V  F  L  V  S  W  R  N  P  D  A  S  M  A  G  S  V  D

1711  CGACTACATCGAGCACGCCGCCATCCGCGCCATCGAAGTCGCGCGACATCAGCGGCCAGGACAAGATCAACGTGCTCGGGCGT    1800
      D  Y  I  E  H  A  A  I  R  A  I  E  V  A  R  D  I  S  G  Q  D  K  I  N  V  L  G  ;  V

1801  GGGCGGCACCATTGTCTCGACCGCCCTGGCCGTGCTGGCCGCGCGCGGCGAGCACCCGGCCGCCAGCGTCACGCTGACCTGCT    1890
      G  G  T  I  V  S  T  A  L  A  V  L  A  A  R  G  E  H  P  A  A  S  V  T  L  T  :  L

1891  GGACTTTGCCGACACGGGCATCCTCGACGTCTTTGTGACGAGGGCCAGTGCGCGAGGCGACGCTGGGCGGCGGGGGCGGC    1980
      D  F  A  D  T  G  I  L  D  V  F  V  D  E  G  H  V  Q  L  R  E  A  T  L  G  G  ;  A

1981  GCCGTGCGCGCTGCTGCGCGGCCTTGAGCTGGCCAATACCTTCTCGTTCTTGCGCCCGAACGACCTGGTGTGGAACTACGTGACAA    2070
      P  C  A  L  L  R  G  L  E  L  A  N  T  F  S  F  L  R  P  N  D  L  V  W  N  Y  V  )  N

2071  CTACCTGAAGGGCAACACGCCGGTGCCGTTCGACCTGCTGTTCTGGAACGGGCGACGCCACCAACCTGCCGGGGCGGTGGTATTACGTGTA    2160
      Y  L  K  G  N  T  P  V  P  F  D  L  F  W  N  G  D  A  T  N  L  P  G  P  W  Y  N  Y

2161  CCTGCGCCACACCTACCTGCAGAACGAGCTCAAGTACCGGGCAAGCTGACCGTGTGCGGTGTGCCGGTGCCGGTGGACCTGGCCAGGACGT    2250
      L  R  H  T  Y  L  Q  N  E  L  K  V  P  G  K  L  T  V  C  G  V  P  V  D  L  A  S  )  V
```

*FIGURE 4 CONT*

```
2251  GCCGACCTATATCTACGGCTCGCGCGAAGACCATATCGTGCCGTGACCGGCCTATGCCTCGACCGCGAACAAGCTGCG  2340
       P  T  Y  I  Y  G  S  R  E  D  H  I  V  P  W  T  A  A  Y  A  S  T  A  N  K  L  R

2341  CTTCGTCCTGGGTGCGTCGGGCCATATCGCCGGTGTGATCAACCCGCCAAGAACAAGCCAGCCAAGATGGCTGCC    2430
       F  V  L  G  A  S  G  H  I  A  G  V  I  N  P  P  A  K  N  K  R  S  H  D  A  L  P

2431  GGAGTCGCCGCAGCAATGGCTGGCCGGCCATCGAGCATCACGGCCAGCTGTGCCGGACTGGACCGCCCGGGCAGGCCGG  2520
       E  S  P  Q  Q  W  L  A  G  A  I  E  H  H  G  S  W  W  P  D  W  T  A  G  Q  A  G

2521  CGCGAAACGCCGCCGCCCGCCAACTATGGCCAATGCGGCTATCGCGAATGAACCCGCGCCTGGGCGAAGCCAAGGCATG  2610
       A  K  R  A  A  P  A  N  Y  G  N  A  R  Y  R  A  I  E  P  A  P  G  R  A  K  A  *

2611  ACGGCTTGCATGAGTGCCGGCCGTGCGTCATGCACGGCCCCGGCAGCCTGCAGGTTCCTCCCGTTTCCAACTACACAATGAC  2700
                                              Pst                              M  T

2701  TGACGTTGTCATCGTATCCGGCGCCGCACCGCGGTCGGCAAGTTTGGCGGCTCGCTGGCCAAGATCC
       D  V  V  I  V  S  A  A  R  T  A  V  G  K  F  G  G  S  L  A  K  I
```

*FIGURE 4 CONT.*

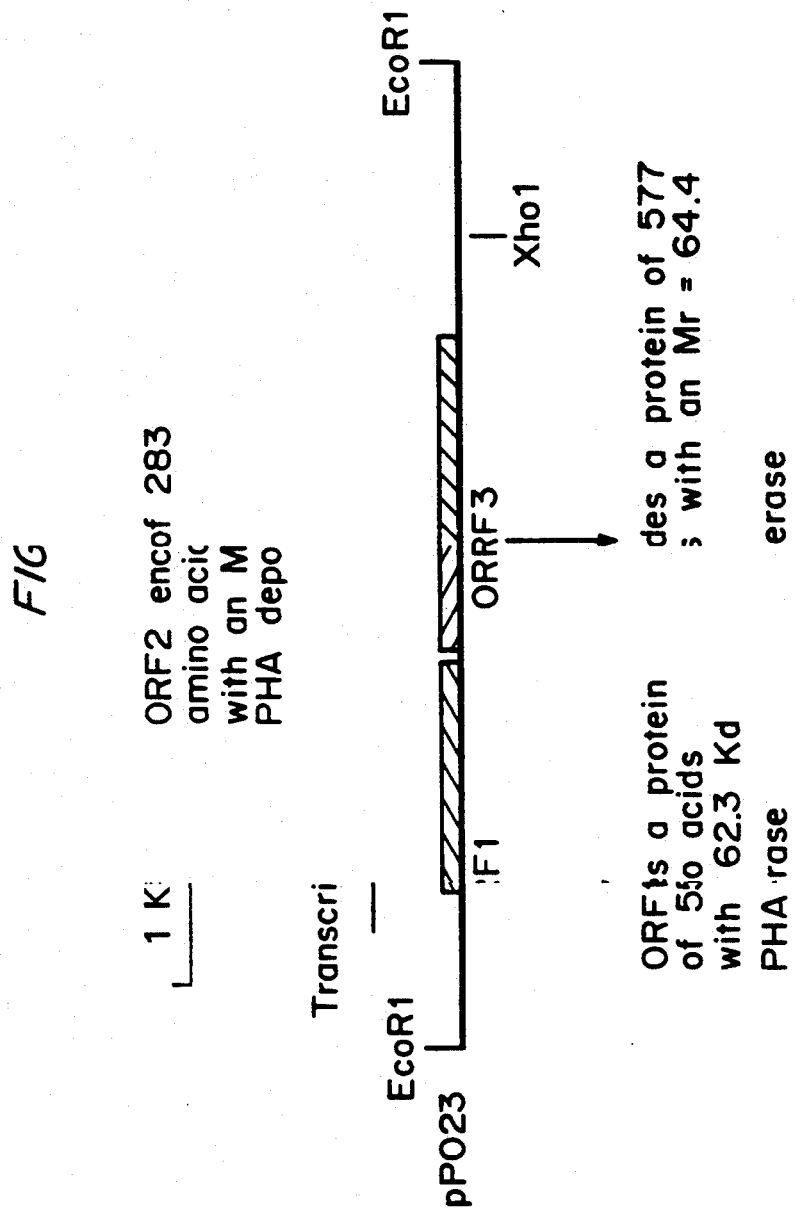

FIGURE 6

```
1171  CAACCCCATCACCGAGCAGGTGCATGCCCGCCTGGTGGTGCCGCAGATCAACAAGTTCTACGTATTCGACCTGATGGA    1260
       N  P  I  T  E  Q  V  H  A  R  P  L  L  V  V  P  P  Q  I  N  K  F  Y  V  F  D  L  M

1261  AAAGAGCCTGGCACGCTACTGCCTGCCTCGCAGCAGGACCTTCATCATCGACCTTCATCAGCTGGAGGCGGACCCAAGCCCAGGCGTGGGG    1350
       K  S  L  A  R  Y  C  L  R  S  Q  Q  Q  T  F  I  I  S  W  R  N  P  T  K  A  Q  R  I  G

1351  CCTGTCCACCTACATCGACGCGCTCAAGGAGGCCGTGCTGGCGATTACCGGCAGCAAGGACCTGAACATGCTGCCCTG    1440
       L  S  T  Y  I  D  A  L  K  E  A  V  D  A  V  L  A  I  T  G  S  K  D  L  N  M  L  C

1441  CTCCGGGGGCATCACCTGCACGGCATTGGTCGGCCACTATGCCGCCCTCGGCGAAAACAAGGTCAATGCCCTGACCCTGCTGAGCGT    1530
       S  G  G  I  T  C  T  A  L  V  G  H  Y  A  A  L  G  E  N  K  V  N  A  L  T  L  L  V

1531  GCTGGACACCACCATGGACAACCAGGTCGCCCTCTTCGTCGACGAGCAGACTTTGGAGGCGCCAAGCGCCACTCCTACCAGGTGT    1620
       L  D  T  T  M  D  N  Q  V  A  L  F  V  D  E  Q  T  L  E  A  A  K  R  H  S  Y  Q  S  V

1621  GCTCGAAGGCAGCGAGATGGCCAAGGTGTTCGCCTGGAACATCGCCTCGATGCGCCTGCGAACTGGGTCAACAACTACTCGG    1710
       L  E  G  S  E  M  A  K  V  F  A  W  H  R  P  N  D  L  I  W  N  I  W  V  N  N  Y  L  G

1711  CAACGAGCCGCCGGTGTTCGACATCCTCTTCTGGAACAACGACACCACCAGGCTGCCAGCGGCGTTCCACGGGGACCTGATCATGTT    1800
       N  E  P  P  V  F  D  I  L  F  W  N  N  D  T  T  R  L  P  A  A  F  H  G  D  L  I  F

1801  CAAGAGCAACCGCCTGACCCGACCAGATGCCCTGGAGGTTTGCGGCACTCCGATCGACCTGTCGCGCCAAGATGAGTTCGTGCCAA    1890
       K  S  N  P  L  T  R  P  D  A  L  E  V  C  G  T  P  I  D  L  K  Q  V  K  C  D  I  L

1891  TGCCGGCCACCAACGACCACATCACCCCGTGGCAGTCATGCTACCGCTCGGCGCACCTGTTCGGCGGCAAGATCGAGTTCGTGACCAA    1980
       A  G  T  N  D  H  I  T  P  W  Q  S  C  Y  R  S  A  H  L  F  G  G  K  I  E  F  V  N

1981  CAGCGGCCACATCCAGAGCATCCTCAACCCGCCAGGCGGCTTCATGAACCGTCCGATGCCCGGTGCACTGGC    2070
       S  G  H  I  Q  S  I  L  N  P  P  G  N  P  K  A  R  F  H  T  G  A  D  R  P  G  D  A

2071  CTGGCAGGAAAACGCCACCAAGCATGCCGACTCCTGGTGCTGCACTGGCAAAGCTGGCTGGGAGCGTGCCGGCGAGCTGAAGGC    2160
       W  Q  E  N  A  T  K  H  A  D  S  W  W  L  H  W  Q  S  W  L  G  E  R  A  G  E  L  K  A

2161  GCCGACCGGCCTGGGCAACCGTGCCTATGCCGCTGGGAGGCATCCCGGGCACTACGTTCACGAGGGTTGAGCTGCAGCGGCC    2250
       P  T  R  L  G  N  R  A  Y  A  A  G  E  A  S  P  G  T  Y  V  H  E  R  *
```

*FIGURE 6 CONT.*

```
2251  ACCTGGGGACGGCCACGGTGTTCATTTCACCCCATGAGTCACGCGCATGC          2300
                                                  M  P

2701  AGGCAAGCCCAAGGTGTTGTGGATGATGGCCAGCCCAGCCCACGGCGTTACGTGCAGCCGTCGCATGTCATCCGCATTGCGCCGACGATGG    2790
      G  K  P  K  V  L  W  M  M  A  S  P  R  R  Y  V  Q  P  S  H  V  I  R  I  A  P  T  :  G

2791  CGGGGCCTTCCGGCGTGACCCGAACTGCCATGCAGCACGCCTCCAAGGTGCGCTCCGGGGCAAGATGGCTACTACTGGTGTT           2880
      G  G  F  R  R  D  P  E  L  A  M  Q  H  A  S  K  V  R  S  G  G  K  M  G  Y  Y  W  ,  F

2881  CGCCGGGCTCGGCTGACCAGCATCCACTGGCTGCACAAGATCCAGCAACCTGTCCTGGCCGGCGACGACCGATCCC                2970
      A  G  L  G  W  T  S  I  H  W  L  H  K  I  Q  Q  P  T  L  V  L  A  G  D  D  D  P  ι  P

2971  GCTGATCAACATGCGCCTGCTGGCCTGGCGATTCCCAATGCCAGCTACACATTATCGACGACGGTCATTGTTCCTGATCGGGC          3060
      L  I  N  M  R  L  L  A  W  R  I  P  N  A  Q  L  H  I  I  D  D  G  H  L  F  L  I  ʀ  A
                                                                                      Cla1

3061  CGAGGCCGTCGCCCGATCATCATGAAGTTCCTTCAGCAAGAACGACAGCGCCCGTCATGCACCCTCGCCCCGGCTTCGGGTAAAT        3150
      E  A  V  A  P  I  I  M  K  F  L  Q  Q  E  R  Q  R  A  V  M  H  P  R  P  A  S  G '

3151  CGATCGGCCCTTCTTGCGGGCGCGCCCGCTCCCACAGGGATGCCCGAACCTGTGGAGCGGGGCATGCCCGCGAAGGTCTAGCC         3240
                                                            M  P  A  K  V  S  A

3241  AAATGGCTTAGACGAGGAGTGTTGCCATGAAAGACAAACCGCCAAGCTTCCCGCCACCAGCATGAACGAGAAC                   3330
      K  W  L  R  R  G  S  V  A  M  K  D  K  P  A  K  G  T  P  T  L  P  A  T  S  M  N  V  N

3331  GCCATCCTCGGCCTGCGCGGTCGTGACCGATTCAGCCGCCAAAGCTCGTCGTCACCCGCTCACTACAT                         3420
      A  I  L  G  L  R  G  R  D  L  I  S  T  L  R  N  V  S  R  Q  S  L  R  H  P  L  H  T  H

3421  CACCCTGTTGGCCCTGGGTGGCCAGCTGGGCCGGCGTGATACTGGGTGACACACCGGCTTCAGCCGAACCCGGCGATCCGCCGCTCGAC    3510
      H  L  L  A  L  G  G  Q  L  G  R  V  I  L  G  D  T  P  L  Q  P  N  P  R  D  P  R  I  D

3511  CCGACATGGAGCCAGAACCCGTTCTACCGGCCTGGCCTGGCCAGAAGCCCGGCCTGTGATCGAAAGC                          3600
      P  T  W  S  Q  N  P  F  Y  R  R  G  L  Q  A  Y  L  A  W  Q  K  Q  T  R  L  W  I  F  S

3601  CACCTGGACGACGATGACGGGCCCGTGCGCACTTCCTGTTCAACCTGATCAACGATGCCCTGGCCAAGAACTGCTGACCCG            3690
      H  L  D  D  D  D  R  A  R  A  H  F  L  F  N  L  I  N  D  A  L  A  P  S  N  S  L  I  P
```

*FIGURE 6 CONT.*

```
3691  CTGGCGGTCAAGGAACTGTTCAACAGCGGTGGCCAGAGCCTGGTGCGCGGTGCCCACCTGCTCGATGACCTGCGCCACACGGC      3780
      L  A  V  K  E  L  F  N  S  G  G  Q  S  L  V  R  G  V  A  H  L  L  D  D  L  R  H  N  G

3781  CTGCCACGGCCAGTCGACGAGCGGCCTTCGAAGTGGGCGGCAACCTGGCCGCGACTGCCCGTGGTGTTTCGCAACGCCTG        3870
      L  P  R  Q  V  D  E  R  A  F  E  V  G  G  N  L  A  A  T  A  G  A  V  V  F  R  N  E  L

3871  GAACTGATCCAGTACAAGCCGATGAGCGAAAAGCAGCACCCCGACTGCTGGTGCCCACAGATCAACAAGTTCTACTTC         3960
      E  L  I  Q  Y  K  P  M  S  E  K  Q  H  A  R  P  L  L  V  V  P  P  Q  I  N  K  F  Y  F

3961  GACCTCAGCTCGACCAACAGCTTCGTCCAGTACATGCTCAAGAATGGCCTGCAGGTGTTCATGGTCAGCTGGCGCAACCCGGCGC    4050
      D  L  S  S  T  N  S  F  V  Q  Y  M  L  K  N  G  L  Q  V  F  M  V  S  W  R  N  P  D  R

4051  CACCCGGAATGGGCCTGTCCAGCTACGTGCAGGCCCTGGAAGAAGCCTCAACGCTTGCCGAGCATTAGCGGCAACCGGCAAC      4140
      H  R  E  W  G  L  S  S  Y  V  Q  A  L  E  E  A  L  N  A  C  R  S  I  S  G  N  R  D  N

4141  CTGATGGGCGCCCTGCGCCGGCGGCCTGACCATGGCCGCGGGCCTGACCATGGCCGCCCTGCAGGGCCACCTGCAGGCCAAGCACCAGCTGCGGCGGGTGCGCGCC   4230
      L  M  G  A  C  A  G  G  L  T  M  A  A  L  Q  G  H  L  Q  A  K  H  Q  L  R  R  V  R  A

4231  ACCTACCTGGTCAGCTTGCTCGACGACAGCAAGTTCGAAAGCCCGGCCAGCCTGTTCGCCGACGAGCAGACCATCGAGGCGCCATCGC      4320
      T  Y  L  V  S  L  L  D  S  K  F  E  S  P  A  S  L  F  A  D  E  Q  T  I  E  A  A  K  R

4321  TCCTACCAGCGCGGTGTCCTGGATGGCGCCGAGGTGGCGCGGATCTTCGCGTGGATGCGGCCCAACGACCTGATCTGGAACTGGTC      4410
      S  Y  Q  R  G  V  L  D  G  A  E  V  A  R  I  F  A  W  M  R  P  N  D  L  I  W  N  Y  V

4411  AACAACTACCTGCTCGGCAAGACACCACCAGCCTTCGACATCCTGTACTGGAACGCCGACAGCACGCGCCTGCCCGCGGCGTGGC     4500
      N  N  Y  L  G  K  T  P  P  A  F  D  I  L  Y  W  N  A  D  S  T  R  L  P  A  A  L  G

4501  GACCTGCTGGACTTCTTCAAGCTCAACCCGCTGACCCACCCGGCTGAGGTATGCGGCACACCATCGACCTGCAGAAGGAG      4590
      D  L  L  D  F  F  K  L  N  P  L  T  H  P  A  G  L  E  V  C  G  T  P  I  D  L  Q  K  E

4591  CTGGACAGTTTCACCGTGCCGGCAGCAACGACCATCACCCCGTGGATGCGGTGTACCGGTCAGCCTTGCTCGGTGACCGG       4680
      L  D  S  F  T  V  A  G  S  N  D  H  I  T  P  W  D  A  V  Y  R  S  A  L  L  G  G  R

4681  CGCTTCGTGCTGGCCAACAGCGGCCACATCCAGAGCATCATCAACCCCGGCAACCCCAAGGCCTACTACCTGGCCAACGCCTG       4770
      R  F  V  L  A  N  S  G  H  I  Q  S  I  I  N  P  P  G  N  P  K  A  Y  Y  L  A  N  I  L
```

*FIGURE 6 CONT.*

```
4771  TCCAGGCGACCCGGTGCTGGCTCCACAGATGCCAAGCGCAGCGAAGGCAGCTGGTGCCGTTGTGGCTGGAGTGATCACCGCGCCC  4860
       S  S  D  P  R  A  W  L  H  D  A  K  R  S  E  G  S  W  W  P  L  W  E  W  I  T  A  R

4861  GGCCCGCTCAAGGCACCGGCCAGCGAACTGGGCACCTACCCGGCCGCCGGGCCACTTACGTGCTGACCCGA  4950
       G  P  L  K  A  P  R  S  E  L  G  N  A  T  Y  P  P  L  G  P  A  P  G  T  Y  V  L  T  R

4951  GCATGCCGACTGGATGAAGAACTCGCGACCGTATCTCGACGTGTTCAACCAGCAGGGCGAACGAACGTATCCCT  5040

5041  GGAAATTGCCAAGGAACTGGGCCATGCCCTGCTCAACCTCTACTACCACTTCCACGGCAAGGAGCCGTTGGTGCTGGGGTTGTTCCG  5130

5131  CTTTGAAGAAGCGCTGATGCCCTTGCTCGACCCCGGCCTGGAGGTACGCGCTGGACGCGGAAGCATTACTGCGTGTCCTGCACCTGGT  5220

5221  CGAACGCATGGGCGCAGTACCGCTTCCGTTCCAGGACCTGTCGAACCTGACCGGCGCCTGCCCAAACTGGGCCGGGCCATGCGGCCT  5310

5311  GATCAACGCGCTCAAGGCGCACACTGGGCGCGGGTTGCTGGCCAGCCTCAAGGGCCAAGGGTTGGTAGAGAGCGAGACCCAGGGCTGCA  5400

5401  ACTGGTGGAGCAGATCACCCTGACACTGATGTTCTCGCTGATTATCAGCGGGTACTGGGGGGATGTGGGGATTGTGTA  5490

5491  CCAGGTGATGATCGTGGCGCCGCAGGCCCGCATCTGCAGGCCCCCGGGGGGGCGAGCAATTGGCGTGCCGGTATCTGGAGGGGGC  5580
                                                    XhoI

5581  CTGTTGATTCGGTGTCGCGGCTTTGCCGGCATGCCCGCCGCTCCCACAGTGAAATGCAGTCTCGAGTGCACACAGGACCTGTGGGGG  5670

5671  GCAAGCCCGCGAAGATGGCGACGCGGTATCAGGATCAGGGCCGTGCTGCTCGTGCCGAAGGCGGGTTGCTGGCCGGAGCCGCGG  5760

5761  GCGCCAACGCTGCGGCTAGCGGCCCGGAGCGGCCGCTGGCCGGCTTGGCCGGCCCGCAGGCTTGGCCGCAGCAGGGTTTAGCCGCGG  5850

5851  CAGGCTTCTTCCGCCACAGCCGGTTTGGCCCGCTCCGGTTTCGCCGCAGGCTTGGCCGGCTCGGCCGTCTTGGCCAGTGGCCTTGGCCGGCCTTGCTAG  5940

5941  CCTTGGCCTGCCGGCTTGGCTCAGTGCCGCACGAGAAATCGGGTAACGGCCAGAAATCGGGGTAACGGAAGCGCCGGTAACGCGAAGGCGGTTGCCACCTGGT  6030

6031  CCGGTTGGCCTGCCTTGATCTCGTTGCGGCTCGGGCACGCCAAGGCGCAGATGGCACTGTTCAGGCGCCTTGTCAGGCGTCTTCGAGTTCC  6120

6121  GCAGGGCCTTGATCTCGTTGCGGCTCGGGCACGCCAAGGCGCAGATGGCACTGTTCAGGCGCCTTGTCAGGCGTCTTCGAGTTCC  6210

6211  ACTTGCCTAGCGCAGGCGTCCTTCACGCCCGACACACGGCGAAGTGTCGACTTGGCAGTTCAGCAAACATCTCTCGGGTCTTC  6300

6301  GCCTGTTTCTCGGCCTTCTCGGCCATCCTTACCAGGCAGTCAGTGAACAGCTTCGGGTCGATCTTCGAATAGATACCACCC  6390

6391  GCCAGCCAGATCTTGCGGGAGTACTTCTCGAATCCCGACCCAGGAGCTGCCTTCTTTCTCGAATTC  6459
                                                                   EcoR1
```

FIGURE 6 CONT.

METHOD FOR PRODUCING NOVEL POLYESTER BIOPOLYMERS

The United States government has rights in this invention by virtue of grants from the National Institute of Health, Office of Naval Research, and National Science Foundation.

BACKGROUND OF THE INVENTION

This is a continuation of copending application Ser. No. 07/378,155 filed on Jul. 10, 1989, which is a continuation-in-part of U.S. Ser. No. 067,695 entitled "Method for Producing Novel Polyester Biopolymers" filed Jun. 29, 1987 by Oliver P. Peoples and Anthony J. Sinskey, both now abandoned.

Synthesis by bacteria has long been the only means for production of many of the more complex biopolymers. Only recently have pathways for the synthesis of these polymers been determined. Much effort has gone into the isolation of the various enzymes and cofactors involved in these pathways. Regulation of their expression has largely been empirical, i.e., the concentration of nutrients or other factors such as oxygen level have been altered and the effect on polymer production and composition measured.

In order to have control over the production of these complex biopolymers, and to modify them in a specific fashion, it is necessary to design a system for determining the chemical steps required for their synthesis; to isolate and characterize the proteins responsible for these chemical steps; to isolate, sequence, and clone the genes encoding these proteins; and to identify, characterize, and utilize the mechanisms for regulation of the rate and level of the expression of these genes.

Polyhydroxybutyrate, a commercially useful complex biopolymer, is an intracellular reserve material produced by a large number of bacteria. Poly-beta-hydroxybutyrate (PHB), the polymeric ester of D(−)-3-hydroxybutyrate, was first discovered in *Bacillus megaterium* in 1925. Both the chemical and physical properties of this unique polyester have made it an attractive biomaterial for extensive study. PHB has a variety of potential applications, including utility as a biodegradable/thermoplastic material, as a source of chiral centers for the organic synthesis of certain antibiotics, and as a matrix for drug delivery and bone replacement. In vivo, the polymer is degraded internally to hydroxybutyrate, a normal constituent of human blood.

The enzymatic synthesis of the hydrophobic crystalline PHB granules from the $C$ biosynthon acetyl-CoA has been studied in a number of bacteria. Three enzymes: beta ketothiolase, acetoacetyl-CoA reductase and PHB polymerase, are involved in the conversion of acetyl-CoA to PHB.

Thiolases are ubiquitous enzymes which catalyze the synthesis and cleavage of carbon-carbon bonds and thus occupy a central role in cellular metabolism. Different thiolase enzymes are involved in terpenoid, steroid, macrolide and other biosynthetic pathways as well as the degradation of fatty acids. In *Z. ramigera*, the condensation of two acetyl-CoA groups to form acetoacetyl-CoA is catalyzed by beta-ketothiolase. The acetoacetyl-CoA is then reduced by an NADP-specific reductase to form D(−)-beta-hydroxybutyryl-CoA, the substrate for PHB polymerase.

Beta-Ketothiolase (acetyl-CoA-CoA-C-acetyltransferase, E. C. 2.3.1.9) has been studied in *A. beijerinckii* (Senior and Dawes, *Biochem. J.*, 134, 225–238 (1973)), *A. eutrophus* (Oeding and Schlegel, *Biochem. J.*, 134, 239–248 (1973)), *Clostridium pasteurianum* (Bernt and Schlegel, *Arch. Microbiol.*, 103, 21–30 (1975)), and *Z. ramigera* (Nishimura et al., *Arch. Microbiol.*, 116, 21–27 (1978)). The cloning and expression of the *Z. ramigera* acetoacetyl-CoA reductase genes was described in U.S. Ser. No. 067,695. This gene was then used as a hybridization probe to isolate the reductase gene from other bacterial species, including *Alcaligenes eutrophus* and *Nocardia*.

The reductase involved in PHB biosynthesis in *Z. ramigera* is stereospecific for the D(−)-isomer of hydroxybutyryl-CoA and uses NADP(H) exclusively as a cofactor. The best characterized Acetoacetyl-CoA reductase is that from Zoogloea, described by Saito et al., *Arch. Microbiol.*, 114, 211–217 (1977) and Tomita et al., *Biochemistry of Metabolic Processes*, 353, D. Lennon et al., editors (Elsevier, Holland, 1983). This NADP-specific 92,000 molecular weight enzyme has been purified by Fukui, et al., *Biochim. Biophys. Acta* 917, 365–371 (1987) to homogeneity, although only in small quantities. As described in U.S. Ser. No. 067,695, the beta-ketothiolase enzyme from *Z. ramigera* has now been cloned, expressed and the product thereof purified to homogeneity. The cloned gene was used to identify and isolate the corresponding beta-ketothiolase gene in other bacterial species, including *Alcaligenes eutrophus* and *Nocardia*.

The PHB polymerase in *Z. ramigera* is stereospecific for D-beta-hydroxybutyryl CoA. Synthetases from other bacteria such as *A. eutrophus* can utilize other substrates, for example, D-beta-hydroxyvaleryl CoA, since addition of propionate into *A. eutrophus* cultures leads to incorporation of $C_5$ and $C_4$ units into a PHB/HV copolymer. Griebel and Merrick, *J. Bacteriol.*, 108, 782–789 (1971) separated the PHB polymerase from native PHB granules of *B. megaterium*, losing all of the enzyme activity in the process. They were able to reconstitute activity only by adding PHB granules to one of two fractions of the protein. More recently, Fukui et al., *Arch. Microbiol.*, 110, 149–156 (1976) and Tomita et al. (1983), investigated this enzyme in *Z. ramigera* and partially purified the non-granule bound PHB polymerase. A method for cloning, expressing and using the product thereof in the synthesis of novel polymers was described in U.S. Ser. No. 067,695.

A whole range of polyhydroxalkanoate (PHA) storage polymers has been found to be produced by bacteria, including *A. eutrophus* and *P. oleovorans*. The PHA polymers are heteropolymers of the D-isomer of β-hydroxyalkanoates with the variation occurring in the length of the side chains ($CH_3-H_8H_{17}$). For example, when grown in the presence of 5-chloropentanoic acid, *A. eutrophus* incorporates 3-hydroxybutyrate, 3-hydroxyvalerate and 5-hydroxyvalerate into the polymer.

Given the extremely high yields of this polymer obtainable through classic fermentation techniques, and the fact that PHB and PHA of molecular weight greater than 10,000 is useful for multiple applications, it is desirable to develop new PHB-like biopolymers to improve or create new applications.

The production of poly-beta-hydroxyalkanoates, other than PHB, by monocultures of *A. eutrophus* and *Pseudomonas oleovorans* was reported by deSmet, et al., in *J. Bacteriol.*, 154, 870–878 (1983). In both bacteria, the polymers were produced by controlled fermentation. *A. eutrophus*, when grown on glucose and propionate, produces a heteropolymer of PHB-PHV, the PHV content reaching approximately 30%. *P. oleovorans* produces a homopolymer of poly-beta-hydroxyoctanoate when grown on octane. Nocardia has been reported to form copolymers of PHB-PH-2-butenoate when grown on n-butane. Determination of the final composition of 3-hydroxybutyrate polymers by controlled fermentation using selected substrates is also disclosed in U.S. Pat. No. 4,477,654 to Holmes et al.

With the availability of a variety of enzymes varying as to their substrate specificity and techniques for expressing the genes encoding the enzymes in other hosts, especially plants, it is possible to provide an economic, biodegradable alternative to the presently available plastics derived from petroleum, especially polypropylene.

It is therefore an object of the present invention to provide further enzymes for use in a method for synthesis of complex biopolymers, particularly PHB, PHA and similar polymers.

It is a further object of this invention to isolate, sequence, and clone additional genes encoding these proteins for polymer synthesis, as well as means for regulation of the rate and level of the expression of these genes.

It is another object of the present invention to provide purified proteins expressed from the genes encoding the proteins for synthesis of polyhydroxybutyrate and polyhydroxyalkanoate.

It is a further object of the present invention to provide methods for using these proteins and regulatory sequences to create novel biopolymers having polyester backbones.

It is a still further object of the present invention to provide an economic source of biodegradable polyhydroxyalkanoates and novel related polymers, using both bacterial and plant cells for production.

SUMMARY OF THE INVENTION

A method for controlling and modifying biopolymer synthesis by manipulation of the genetics and enzymology of synthesis of polyhydroxybutyrate (PHB) and polyhydroxyalkanoate (PHA) polyesters at the molecular level in procaryotic and eukaryotic cells, especially plants.

Examples demonstrate the isolation, characterization, and expression of the genes involved in the production of PHB and PHA polymers. Genes encoding the enzymes in the PHB and PHA synthetic pathway (beta-ketothiolase, acetoacetyl-CoA reductase and PHB polymerase or PHA polymerase) from *Zoogloea ramigera* strain I-16-M, *Alcaligenes eutrophus*, *Nocardia salmonicolur*, and *Pseudomonas olevorans* were identified or isolated and expressed in a non-PHB producing organism, *E. coli*.

In a preferred embodiment using bacterial cells, the polymer is made in *A. eutrophus* due to its capacity for accumulating PHB up to 70 to 80% dry cell weight under conditions of nitrogen or phosphate limitation. In another embodiment, the genes are introduced into plant cells for expression and synthesis of PHB, PHA, and novel polymers. Specific modifications to the polymers include variation in the chain length of the polymers and incorporation of different monomers into the polymers to produce co-polymers with different physical properties.

BRIEF DESCRIPTION OF THE DRAWINGS

FIG. 1 is the thiolase gene sequence from *Zoogloea ramigera*. The sequences located at positions homologous to the *E. coli* "-10" and "-35" concensus regions (-100 to -95 and -122 and -116) upstream from the transcription start site (bold arrow) are underlined. A probable ribosome binding site is underlined (-11 to -8).

FIG. 2 is the complete nucleotide sequence of 2.3 kb of *Z. ramigera* DNA located downstream from the thiolase gene in clone pUCDBK1, encoding the acetoacetyl CoA reductase. The sequence of 2094 bp extending from the first Sal1 site to the second Sma1 site is shown. Also shown is the translation product of the acetoacetyl-CoA reductase structural gene extending from the ATG at nucleotide 37 to the TGA stop codon at nucleotide 760. Boxed amino acid residues 2 to 6 are identical to those obtained by Edman degradation of the purified protein. A potential ribosome binding site is underlined and a potential transcription terminator is indicated by arrows. Restriction sites for Sal1 and Sma1 are shown.

FIG. 3 shows the nucleotide sequence of a corresponding 2 kb fragment *A. eutrophus* DNA cloned in plasmid pAeT3. The translation products of the *A. eutrophus* thiolase and acetoacetyl-CoA reductase genes extending from nucleotides 40 to 1219 and 1296 to 2034, respectively, are shown. Restriction endonuclease cleavage sites used in the construction of the overproduction vectors pAT and pAR are shown. Pst 1=Pst 1; Ava=Ava 2 and Dde=Dde 1.

FIG. 4 is the nucleotide sequence of the PHB polymerase (phbC) locus of *Alcaligenes eutrophus* H16. The translation product of the open reading frame from position 842 to position 2608, the predicted amino acid sequence of PHB polymerase is shown. Also shown is the translation product of the first 72 nucleotides of the phbA gene. A sequence capable of forming a hairpin structure (position 2660) is indicated by the arrows.

FIG. 5 shows the potential coding regions of the *P. oleovorans* PHA polymerase gene, open reading frames ORF1, ORF2, and ORF3. ORF1 begins at the ATG initiation codon nucleotide 554 and ends at the TGA stop codon nucleotide 2231 and encodes a polypeptide of 562 amino acids with an $M_r=60,000$. ORF2 begins at the ATG position 2297 and ends at the TAA position 3146. ORF2 begins at the ATG position 3217 and ends at the TGA position 4948.

FIG. 6 is the nucleotide sequence analysis of the polymerase structural gene (FIG. 6a) and ORF3 (FIG. 6b) from the 6 kb fragment containing the *P. oleovorans* phbC gene.

DETAILED DESCRIPTION OF THE INVENTION

The following methods were used to isolate genes encoding beta-keto thiolase, acetoacetyl-CoA reductase, PHB polymerase, and PHA polymerase, and their expression products, to identify and characterize sequences regulating their expression, and to determine the effect of culture conditions and substrate availability on polymer production. Techniques for constructing systems for the production of PHB and PHA-like biopolymers are also disclosed. By combining these enzymes in either bacterial or plant cells with the appropriate substrates under controlled culture conditions of available oxygen and temperature, a variety of polymers can be constructed. The enzymes or nucleotide sequences controlling their expression can also be modified to alter the quantity of expression or substrate specificity to further vary the resulting polymers. An added advantage is that substrates which normally cannot be used with whole cells can be manufactured using the isolated enzymes.

The methods, genes, and products of their expression and polymer synthesis are described in detail in the following non-limiting examples.

Media and Culture Conditions

Zoogloea ramigera strain I-16M (ATCC 19623) was used initially to study the genetics of the PHB biosynthetic pathway. Z. ramigera DNA was purified from 200 ml mid-log phase cultures as follows: cells were harvested by centrifugation, washed in 20 mM Tris-HCl, pH 8.2, and resuspended in 10 ml of Tris-HCl. The cells were then spheroplasted by the addition of 10 ml of 24% w/v polyethylene glycol 8000 and 2 ml of 25 mg/ml lysozyme, followed by incubation at 37° C. for 30 min. The spheroplasts were harvested by centrifugation, resuspended in 5 ml of TE buffer (10 mM Tris-HCl, pH 8.0, 1 mM EDTA), 300 microliters of 10% w/v SDS added, and the cells lysed by incubating at 55° C. for 10 min. An additional 10 ml of TE was added and the lysate incubated with RNAse (50 microgram/ml) and proteinase K (30 microgram/ml) for 1 h at 37° C. The DNA was then purified by CsCl gradient centrifugation.

E. coli strains were grown in LB (Luria Bertani) medium, (NaCl, 10 gl; Tryptone, 10 g/l; yeast extract, 10 g/l ) or 2XTY medium (NaCl, 5 g/l; Tryptone, 16 g/l; yeast extract, 10 g/l ). For the production of PHB or PHA by E. coli containing recombinant plasmids, minimal media was used, with the modification that the $(NH_4)_2SO_4$ concentration was decreased to 0.04%.

A. eutrophus strains were grown in Trypticase soy broth (TSB, BBL Microbiology systems, Cockeysville, Md.) or a defined minimal medium composed of 0.39 g/l $MgSO_4$; 0.45 g/l $K_2SO_4$; 12 ml 1.1 m $H_3PO_4$; 15 mg/l $FeSO_4.7H_2O$; 24 ml trace elements (20 mg/l $CuSO_4.5H_2O$; 100 mg/l $ZnSO_4.6H_2O$; 100 mg/l $MnSO_4.4H_2O$; 2.6 g/l $CaCl_2.2H_2O$). The pH was adjusted to 6.8 with NaOH and the medium sterilized by autoclaving. $NH_4Cl$ was added to a final concentration of 0.1% or 0.01% as nitrogen source and fructose was added to a final concentration of 0.5-1% (w/v).

Plasmid DNA preparations were carried out using the method of Birnboim and Doly in Nucleic Acids Res., 7, 1513-1523(1979) as described by Ish-Horowicz and Burke, Nucleic Acids Res., 9, 2989-2998 (1981). Lambda DNA was prepared by standard procedures described in Maniatis et al., Molecular Cloning: A Laboratory Manual. (Cold Spring Harbor Laboratory, Cold Spring Harbor, N.Y. 1982). DNA sequence analysis was carried out using the M13mp18 and M13mp19 cloning vectors (Yanisch-Perron, et al., Gene 33,103-109 (1985)) and the dideoxy chain termination procedure of Sanger, et al., Proc. Natl. Acad. Sci. USA 74, 5463-5467 (1977). $\alpha$-[$^{35}$S]-dATP and the Klenow fragment of DNA polymerase 1 were purchased from Amersham. Sequence data were compiled and analysed on a VAX system.

A recombinant library of random Z. ramigera chromosomal DNA fragments was constructed using the lambda gt11 expression vector described by Young and Davis, Science, 222, 778-782 (1983). Z. ramigera DNA was first methylated using EcoRI methylase and then partially digested with DNAse 1 in the presence of $Mg^{2+}$, as taught by Anderson, Nucleic Acids, 9, 3015-3026 (1981). The ends of the partially digested DNA fragments were repaired using Klenow polymerase, EcoRI linkers added, and the DNA digested to completion with an excess of EcoRI. Fragments of 2-8 kb were size-selected on a 1.5% agarose gel, purified by electroelution, and ligated with EcoRI-digested phosphatased lambda gt11 DNA. Ligations were carried out for 18 h at 4° C. using 2 micrograms of lambda gt11 DNA and 1 microgram of fragmented chromosomal DNA in a total volume of 10 microliters. The complete ligation reactions were packaged in vitro using lambda extracts prepared from E. coli strains BHB2688 and BHB2690, Hohn and Murray, Proc. Natl. Acad. Sci., USA, 74, 3259-3263 (1977), as described by Maniatis et al. (1982). Packaged phage were plated out and amplified on E. coli Y1088.

Screening of the lambda gt11 expression library was carried out using rabbit anti-thiolase antibodies and a modification of the procedure described by Young and Davis, Science, 222, 778-782 (1983).

Restriction endonucleases, T4 DNA ligase and DNA polymerase 1 were obtained from New England Biolabs and used under conditions provided by the manufacturer. Calf intestinal alkaline phosphatase was purchased from Boehringer Mannheim Corporation. All routine DNA manipulations, including plasmid purifications, E. coli transformations, etc. were performed using methods described by Maniatis, et al. (1982). Chromosomal DNA was purified from A. eutrophus strains, grown to late logarithmic phase in TSB. Transfer of restriction digested DNA samples from agarose gels to nitrocellulose filters, prehybridization and hybridization with $^{32}$P-labelled DNA probes was as described by Peoples, et al., J. Biol. Chem. 262, 97-102 (1987). Rapid plasmid isolation from A. eutrophus recombinant strains for restriction analysis were performed by the alkaline extraction procedure of Birnboim and Doly, Nucleic Acids Res. 7, 1513-1523 (1979).

Conjuqation in A. eutrophus

The conjugal transfer of the broad host range plasmid, pLAFR3, or recombinant derivatives of pLAFR3, into A. eutrophus was performed using the method described by Easson et al, J. Bacteriol. 169, 4518-4524 (1987). In this case, however, the recipient A. eutrophus cells were not sonicated and transconjugants were selected on A. eutrophus mineral agar plates containing 0.01% $NH_4Cl$ as nitrogen source, 1% (w/v) fructose as carbon source and 10 $\mu g$/ml tetracycline.

For Tn5 mutagenesis, a spontaneous streptomycin resistant strain of A. eutrophus 11599 (1599 S1) was used. Transfer of pRK602 (Tn5) was carried out as described above using E. coli MM294A (pRK602) as the only donor. A. eutrophus strains containing Tn5 were selected for by growth on streptomycin (500 $\mu g$/ml) and kanamycin (100 $\mu g$/ml).

Identification of the Z. ramigera Thiolase gene

Thiolase antiserum was prepared in New Zealand White female rabbits, using purified thiolase protein by standard procedures. Antibody titer was estimated by the Ouchterlony double-diffusion assay, Acta Pathol. Microbiol. Scand. 26, 507-515(1949). Purified antibody was prepared from the serum by chromatography on protein A agarose according to Bighee et al., Mol.

*Immunol.* 20, 1353–1357 (1983). Approximately 4×10⁴ recombinant phage adsorbed to *E. coli* Y1090 were plated out on 15 cm LB-agar plates and incubated at 42° C. for 3 h. The plates were then overlayed with nitrocellulose filters (Schleicher & Schull, BA85), which had previously been saturated in 10 mM IPTG, and incubated a further 4 h at 37° C. Filters were removed, washed for 10 min in TBST (50 mM Tris-HCl, pH 7.9, 150 mM NaCl, 0.05% Tween-20), incubated in TBST plus 20% v/v fetal calf serum for 30 min, and rinsed in TBST. First antibody was bound by incubating the filters in 10 ml TBST plus purified anti-thiolase antibody (10 microliters) for 1 h at room temperature. The filters were subsequently washed in three changes of TBST for 5 min each time. Bound first antibody was detected using a biotinavidin horseradish peroxidase detection system (Clontech Laboratories) and horseradish peroxidase color development reagent (Bio-Rad Laboratories, Richmond, Va.).

Proteins were separated by sodium dodecyl sulphate-polyacrylamide gel electrophoresis according to the method of Laemmli, *Nature* 222, 680–685 (1970) and electrophoretically transferred to nitrocellulose filters (Schleicher & Schuill BA85), essentially as described by Burnette, *Anal. Biochem.* 112, 195–203 (1981). Following transfer overnight at 30 V, filters were rinsed in TBS (TBST without Tween-20) and incubated in TBS plus 5% bovine serum albumin. Proteins reacting with anti-thiolase serum were then detected by incubating the filters in 100 ml of TBS, 1% gelatin containing 2 ml of anti-thiolase serum for 1–2 h. Bound first antibody was subsequently detected using goat anti-rabbit IgG horseradish peroxidase conjugate and horseradish peroxidase color development reagent (Bio-Rad Laboratories, Richmond, Calif.).

DNA blots were prepared using DNA fragments separated on agarose gels by the sandwich blot method of Smith and Summers, *Anal. Biochem.* 109, 123–129 (1980) based on the technique developed by Southern, *J. Mol. Biol.*, 98, 503–517 (1975). Filters were hybridized with DNA probes labeled to a high specific activity (0.1–1×10⁸ cpm/μg of DNA) with [α-³²P]dATP, by nick translation, Rigby et al., *J. Mol. Biol.*, 113, 237–251 (1977). Prehybridizations and hybridizations were carried out at 65° C. in sealed polythene bags. The prehybridization/hybridization solution contained 5×SSCP (1×SSCP contains 0.15 M NaCl, 0.15 M sodium citrate, 10 mM Na₂HPO₄, 10 mM NaH₂PO₄), 5×Denhardt's solution, 0.1% (w/v) SDS, 10 mM EDTA, and 100 μg/ml sonicated denatured salmon DNA. Filters were prehybridized for 8–18 h and hybridized for 16–18 h using 10⁷ cpm of labeled DNA probe per filter.

Lysogens of lambda gt11 recombinant clones were prepared in *E. coli* Y1089 as described by Young and Davis, *Science* 222, 778–782 (1983). For the preparation and analysis of lambda-coded proteins, lysogens were grown at 30° C. in LB (100 ml) until they reached an OD₆₀₀ of 0.5. The prophage was induced by a 20 min incubation at 45° C., IPTG added to 5 mM and the induced lysogens incubated at 37° C. for 1 h. Cells were harvested, resuspended in assay buffer (0.1 M Tris-HCl, pH 7.5, 5 mM beta-mercaptoethanol, 5% (v/v) glycerol), lysed by sonication, cell debris pelleted by centrifugation, and the cell extracts stored at −20° C. The protein concentrations of bacterial lysates were assayed by the method of M. M. Bradford in *Anal. Biochem.* 72, 248–254 (1976), using bovine serum albumin as a standard. Thiolase-enzyme assays were performed as described by Nishimura, et al., *Arch. Microbiol.* 116, 21–27 (1978).

DNA fragments were cloned into the M13 vectors mp10 and mp11 and sequenced by the dideoxy chain-termination method of Sanger et al., *Nucleic Acids Res.* 10, 141–158 (1980), *Proc. Natl. Acad. Sci. USA* 74, 5463–5467 (1977). The M13 sequencing primer and other reagents were purchased from Amersham Corp. G/C rich regions were resequenced using dITP in place of dGTP as described by Mills and Kramer, *Proc. Natl. Acad. Sci. USA* 76, 2232–2235 (1979). Computer-assisted sequence analysis was accomplished using the Staden programs. *Acids Res.* 10, 141–158 (1984).

Approximately 2×10⁵ recombinants were obtained from 1 μg of purified target DNA, and amplified in *E. coli* Y1088. A total of 10⁵ amplified phage were screened using purified rabbit anti-thiolase antibodies. The initial screening identified 10 potentially positive clones (LDBK1–LDBK10). Analysis by restriction digestions demonstrated that clones LDBK2-10 are identical. Clones LDBK1 and LDBK2 were selected for further study. LDBK1 has an insert composed of 2 EcoRI fragments of 3.6 kb and 0.75 kb. LDBK2 has an insert composed of 3 EcoRI fragments of 1.65 kb and 1.08 kb.

The proteins coded for by the LDBK1 and LDBK2 insert sequences were analyzed both for thiolase-enzyme activity and for cross-reaction to rabbit anti-thiolase serum. Lysogenic strains of *E. coli* Y1089 containing LDBK1 and LDBK2 phage DNA were prepared. Several lysogens were obtained for each clone and two of these, Y1089/LDBK1 and Y1089/LDBK2, were used for subsequent studies. A lysogen of the lambda gt11 vector, BNN97/lambda gt11, was used as a control. The results of the thiolase-enzyme assays clearly indicate that the proteins from Y1089/LDBK1 contain a substantial amount of thiolase activity. Furthermore, the thiolase activity is inducible, greater than 5-fold, by the addition of IPTG. This shows that expression of the thiolase-coding sequences is under the transcriptional control of the lac promoter contained in the lambda gt11 vector. Neither the Y1089/LDBK2 nor the BNN97/lambda gt11 protein lysates demonstrate any significant thiolase-enzyme activity even when induced with IPTG.

The size of the proteins responsible for the initial positive reaction to rabbit anti-thiolase antibodies was investigated by Western blot experiments. Protein lysates were separated by SDS-polyacrylamide gel electrophoresis, transferred to nitrocellulose filters, and screened with rabbit anti-thiolase serum. The results show an immunoreactive 40,000 dalton protein in both the IPTG-induced and non-IPTG-induced lysate of Y1089/LDBK1.

The LDBK1 insert was restriction mapped. The large 3.6 kb EcoRI fragment, containing the complete thiolase gene region, was subcloned into the plasmid vector pUC8 for ease of manipulation. Restriction analysis of one of the subclones obtained, pUCDKB1, confirmed the restriction map of this fragment in LDBK1. pUCDKB1 DNA was labeled to a high specific activity with ³²P and hybridized to nitrocellulose filters containing *Z. ramigera* chromosomal DNA digested with the same enzymes used to restriction map pUCDBK1. Southern hybridization experiments confirm that the 5.4 kb genomic fragment hybridizes to both a 1.45 kb SalI/EcoRI and 1.05 kb SalI fragment from pUCDBK1. Based on the result of Southern hybridization experiment, the cloned pUCDBK1 insert is represented in the *Z. ramigera* genome only once.

DNA sequence analysis of the pUCDBK1 insert was carried out using the M13/Sanger dideoxy chain termination method. To locate the gene-coding region, individual DNA sequences were scanned in all six reading frames for homology to the NH$_2$-terminal amino acid sequence. By using this approach, the gene-coding region within the 1.45 kb EcoRI/Sal I fragment was identified. The complete nucleotide sequence of the plus strand of the gene is shown in FIG. 1. 290 bp downstream from the EcoRI site lies the start of the thiolase structural gene, assigned by comparing the DNA sequence to the NH$_2$-terminal amino acid sequence. The NH$_2$-terminal sequence lies in the single long open reading frame which extends from position $-89$ to the stop codon (TAG) at nucleotide 1174. Beginning with a serine and extending for 25 residues, the experimentally determined NH$_2$-terminal sequence aligns identically with residues 2 through 26 of the translated DNA sequence. Translation of the DNA sequence was then used to deduce the remaining amino acid sequence from residue 27 to 391 (nucleotides 79 to 1173). Hence, translation of the DNA sequence from nucleotide 1 to 1174 (in this reading frame) encodes a 391-amino acid polypeptide with a calculated $M_r$ of 40,598. This value is in very good agreement with that of $M_r=42,000$ determined by SDS-polyacrylamide gel electrophoresis.

Two additional pieces of evidence confirm that this translation produce is the correct amino acid sequence of thiolase. First, a search of the predicted amino acid sequence for the active site peptide (NH2-Gly-Met-Asn-Gln-Leu-Cys-Gly-Ser-Gly-COOH) located this peptide at residues 84–92. Finally, the predicted amino acid composition from the translation product and that determined experimentally are in excellent agreement. The G/C content of the 1.46 kb EcoRI-Sa1I fragment is high, 66.2%. When considered separately, the 5'-flanking 290 bp has a G/C content of 57.4% and the structural gene region 68.4%. The amino acid sequence confirms that the *Z. ramigera* thiolase contains 5 cysteine residues. The *Z. ramigera* active site cysteine is at residue Cys-89. Additional cysteines which may be involved in inter- or intradisulphide bonds are Cys-125, Cys-323, Cys-377, and Cys-387. NH$_2$-terminal sequence analysis indicated a serine at position 1.

Seven nucleotides upstream from the ATG start codon is a potential ribosome-binding site, 5'-CTGAGGA-3', identified by homology to the *E. coli* sequence. Additional start codons including two GTGs which can initiate translation in some bacterial genes are located further upstream. Examination of the 5'-flanking region for homology to the "-10" and "-35" *E. coli* promoter elements, identified a potential "-35" region at residues -122 to -116 and a corresponding "-10 region", 5'-TATAAT-3', at position -100 to -95. A poly(T) tract at position -255 to -266 is also present. It is clear that the only post-translational processing of thiolase is the removal of the N-formylmethionine residue, as alternate start codons, ATC or GTG, are either out of frame or have an in-frame stop codon before the start of the structural gene.

The 1.5 Kb Sa11-EcoR1 fragment from pUCDBK1 contains the entire *Z. ramigera* thiolase structural gene plus 283 bp of 5'/flanking DNA. A series of plasmid constructions were made in which this DNA fragment was inserted into the tac promoter vector pKK223-3 (or derivatives thereof). pZT3 was made by cleaving pUCKBK1 with Sa11, blunt-ending with Klenow polymerase and adding on EcoR1 linkers. Following digestion with EcoR1, the 1.5 Kb fragment was purified from an agarose gel and inserted into the EcoR1 site of pKK223-3. Recombinant clones having the gene inserted in the correct orientation with respect to the tac promoter were identified by restriction analysis following transformation of *E. coli* JM105.

A series of clones deleted of sequences in the 283 bp flanking the 5' end of the thiolase gene was then constructed. pUCDBK1 DNA was digested with EcoR1 and treated with Ba131 nuclease. Following Sa11 digestion, the ends of the fragments were repaired with Klenow and EcoR1 linkers added on. The plasmid DNA was cleaved with EcoR1 and fragments in the correct size range, 1.2–1.4 kb, purified from an agarose gel and ligated into the EcoR1 site of pKK223-3. Clones of interest were identified by restriction mapping and the extent of the 5'-deletion determined by DNA sequencing. From this series of clones, pZT3.1-pZT3.5, the clone with the largest deletion, pZT3.5, had 84 bp of the 5'-flanking DNA remaining and therefore a subsequent Ba131 deletion experiment was carried out as follows: pZT3.5 DNA was digested to completion with EcoR1 and treated with Ba131 nuclease; the ends were repaired using Klenow polymerase and EcoRI linkers ligated on, following digestion to completion with EcoR1 and BamH1, fragments corresponding to the NH$_2$-terminal region of thiolase were eluted from an agarose gel, ligated with BamH1 - EcoR1 digested M13mp 11 DNA and plated out on *E. coli* JM101; single-stranded DNA was prepared from 50 transformants and the extent of the 5'-deletion analyzed by T-tracking; double-stranded DNA was prepared, in vitro, from clones of interest and the EcoR1 - Bam1 inserts recovered by restriction digestion and elution from an agarose gel.

In order to reconstruct the intact thiolase gene, the 290 bp BamH1 - HindIII fragment from pZT3.5 was ligated into a vector (pKK226) derived from pKK223-3 by deleting the BamH1 site upstream from the tac promoter; this C-terminal vector was subsequently used for the reconstruction of the Ba131 deleted NH$_2$-termini of interest; clones pZT3.5.1 and pZT3.5.2 were used in subsequent studies.

The effect of deleting sequences in the 283 bp of DNA flanking the thiolase ATG translation initiation codon was determined by analyzing the level of thiolase activity produced by plasmids pZT3.1–pZT3.5.2. 100 ml cultures of the *E. coli* JM105 containing each plasmid were induced with IPTG for 15 hours and the level of thiolase assayed. The most notable feature of these results is the very high level of thiolase expression obtained with clones pZT3.3–pZT3.5.2, the maximum obtained being 178 U/mg for pZT3.5. This represents an increase of 5.9-fold as compared to plasmid pZT3 which contains the entire 283 bp of 5'-flanking DNA. The data demonstrate that the thiolase 5'-flanking sequences located between -84 (pZT3.5) and -168 (pZT3.2) strongly inhibit the expression of the thiolase gene from the tac promoter. The location of these sequences can be narrowed down to the region between -84 (pZT3.5) and -124 (pZT3.4) as the deletion of this region results in the maximum level of tac-directed thiolase expression. Further deletions to -37 (pZT3.5.1) and -26 (pZT3.5.2) do not increase the level of thiolase expression, and in fact a slight decrease is observed. It is important to note that the time course of induction for this series of clones follows the same kinetics as pZT3 and is not appreciably affected by the deletions.

In order to determine if the thiolase promoter lies in the region -84 (pZT3.5) to -124 (pZT3.4), S1 nuclease protection experiments were carried out according to the method of Berk and Sharp, *Cell* 12, 721-732 (1977) on *Z. ramigera* RNA. Total RNA was isolated from a 100 ml mid-log phase culture by the hot phenol/glass beads extraction procedure of Hinnenbusch et al., *J. Biol. Chem.* 258, 5238-5247 (1983). 5'-$^{32}$P-labelled DNA probe was prepared as follows: 10 μg, plasmid pZT3.1 DNA was digested to completion with AvaI and subsequently treated with CIP; the AvaI restriction fragments were labelled at the 5'-end with [gamma-$^{32}$P]-ATP and polynucleotide kinase; following EcoR1 digestion, the DNA was separated on an 8% acrylamide gel and the $^{32}$P-labelled 280 bp probe fragment eluted and recovered by ethanol precipitation. Probe (10,000 cpm) and 11 μg RNA were pooled, freeze dried, resuspended in 10 μg hybridization buffer (40 mM pipes, pH 6.4; 1 mM EDTA, pH 8.0; 0.4 M NaCl; 80% (v/v) formamide), denatured for 10 min at 90° C. and annealed at 55° C. overnight. 235 microliters ice-cold S1 nuclease buffer (0.25 M NaCl; 30 mM NaOAc; 1 mM ZnSO$_4$; 200 μg single stranded calf thymus DNA) containing 2000 units of S1-nuclease was added followed by an incubation at 37° C. for 30 min. The reaction mixture was extracted once with phenol-chloroform and ethanol precipitated in the presence of 0.2 M NaOAc and 10 μg yeast tRNA carrier. The resulting fragments were analyzed on a 6% (w/v) acrylamide, 7 M urea DNA sequencing gel. For size standards, the Maxam Gilbert G and C sequencing reactions were performed on 50,000 cpm of 5'-$^{32}$P-labeled probe DNA. The results clearly show a protected fragment and that the RNA start site is located at the C or T residue, position -86 or -87. A control indicates that in the absence of *Z. ramigera* RNA, the probe is completely degraded, demonstrating the presence of the thiolase promoter regions approximately 10 bp (-96) and 35 bp (-121) upstream. The 5'-untranslated region of the thiolase is 86 bp long.

From the results of the induction experiments, it is clear that the thiolase gene can be expressed at high levels in a soluble, catalytically active form in *E. coli*. S1-nuclease studies map the transcription start site for the thiolase gene in *Z. ramigera* at nucleotides -86/-87. Studies have demonstrated that although the "-35" region of the thiolase promoter is recognized and binds the RNA polymerase, it is the "-10" region which determines the rate of transcription initiation. In the case of pZT3, for example, the simultaneous binding of an RNA polymerase molecule to both the bector and insert promoters would result in the rapid initiation of transcription from the tac promoter which would subsequently be impeded by the presence of the polymerase molecule bound at the Zoogloea promoter. The closer the two promoters are linked, the less chance of polymerase binding to both at the same time and the lower the inhibition. Therefore, this represents one means for controlling rate of expression of the enzyme.

Identification of the *Z. ramigera* Reductase gene

After identifying the promoter region of the thiolase gene and noting the absence of any potential terminator sequences downstream from the thiolase TAG stop codon, the remaining 2 kb of Zoogloea DNA present in clone pUCDBK1 was sequenced and examined for the reductase gene. A series of expression plasmids (pZT1-pZT3) containing either the entire pUDCBK1 insert or fragments thereof were constructed in the *E. coli* tac promoter vector pKK223.3. Each plasmid has the thiolase gene located in the correct orientation for expression from the tac promoter. It is reasonable to expect the tac promoter to direct not only thiolase expression but the expression of any genes located in the 2.3 kb downstream in an operon-like type organization. Clone pZT1 was constructed by inserting the entire 3.8 kb EcoR1 *Z. ramigera* DNA insert from pUCDBK1 into the EcoR1 site of the vector pKK223-3. Subsequently, pZT2 was derived from pZT1 in a straightforward manner by deleting the 850 bp SmaI fragment. pZT3 is constructed as described for the identification of the thiolase promoter. A series of tac promoter induction experiments were performed on each of the recombinant clones pZT1, pZT2 and pZT3. The vector pKK223-3 was used as a control.

*E. coli* cells containing each of the plasmids were grown and induced by the addition of isopropyl-beta-D-galactopyranoside (IPTG) to a final concentration of 2 mM. After 15 h induction, 10 ml cultures were harvested and lysed by sonication. The cell lysates from each clone were then analyzed both by enzyme assay and on SDS-PAGE. No PHB polymerase activity was detected in any of these lysates. Each of the three recombinant plasmids pZT1, pZT2 and pZT3 demonstrate substantial levels of thiolase activity. In addition, the lysates from pZT1 and pZT2 have comparably high levels of AcAc-CoA reductase activity using NADPH as the cofactor. No reductase activity is detected in any of the lysates when NADH is used as a cofactor. The control, pKK223-3, has neither thiolase nor reductase activities. To confirm that the lysates from pZT1 and pZT2 do in fact contain the correct reductase, these lysates were also assayed for oxidation of D(—)beta-hydroxybutyryl-CoA. In both cases, enzyme activity was observed with NADP as electron acceptor.

Each of the lysates described above was also analyzed by SDS-PAGE. The results show the presence of the thiolase protein at around 42,000 daltons in protein lysates from pZT1, pZT2 and pZT3, which is not present in the control, pKK223-3. Lysates of pZT1 and pZT2 also have a small, 25,000 dalton protein which is not present in the lysate of pZT3 or the control, which corresponds to the AcAc-CoA reductase. The results demonstrate that the AcAc-CoA reductase gene is located downstream from the thiolase gene. The entire structural gene for this enzyme must be located between the 3'-end of the thiolase and the first SmaI site downstream in pUCDBK1.

Identification of the Translation Start Site and Overexpression of the Reductase Gene The complete nucleotide sequence of the 2339 bp located 2.3 kb downstream from the first SalI site in pUCDBK1 is shown in FIG. 2. Computer analysis of the sequence data, using codon usage information from the thiolase gene as a standard, identified three open reading frames. N-terminal protein sequence data was obtained from the 25,000 dalton band present in induced lysates from pZT1 and pZT2 following preparative SDS-PAGE and electroelution. This data was used to confirm the translation start site for the corresponding gene. The N-terminal five amino acids determined experimentally match residues 2 through 6 predicted from the DNA sequence of the first open reading frame. Translation of this reading frame predicts a polypeptide of 25,000 molecular weight. The translation product of the first open reading frame starting at the ATG, nucleotide 37 and ending at the TGA stop codon nucleotide is shown in FIG. 2. This is the predicted primary amino acid sequence of the acetoacetyl-CoA reductase protein.

It is evident that the acetoacetyl-CoA reductase gene in clones pZT1 and pZT2 can be expressed at reasonably high levels in *E. coli*. However, in both of these cases, the expression of the reductase gene from the tac promoter is not optimum due to the presence of the thiolase structural gene and 5'-flanking sequence. A simpler acetoacetyl-CoA reductase overproduction vector, pZR14, was constructed. pUCDBK1 DNA was digested to completion with Sal1 and Sma1 and the Sal1 ends repaired using the Klenow fragment of DNA polymerase. Following the addition of EcoR1 linkers and digestion with EcoR1, the fragments were separated by agarose gel electrophoresis. The 1.05 kb fragment corresponding to the acetoacetyl-CoA reductase structural gene plus 36 bp flanking the 5'-end and 266 bp flanking the 3' end was purified and ligated into the EcoR1 site of pKK223-3. pZR14 was then identified as having the correct restriction map with the reductase gene in the right orientation. Induction experiments were performed on pZR14 as described for pZT1, pZT2 and pZT3. Acetoacetyl-CoA reductase was expressed.

Identification of the Thiolase and Reductase Genes in *A. eutrophus*

The methods used in isolating the first two PHB genes from Zoogloea were applied to the identification, isolation and characterization of gene from another PHB producing species, *Alcaligenes eutrophus*, using the Zoogloea thiolase gene region as a hybridization probe to locate homologous sequences.

Subsequent sequence analysis of a 2 kb Pst1 fragment of *A. eutrophus* DNA cloned into pUC8 (clone pAeT3) identified the corresponding thiolase gene region in the *A. eutrophus* H16 genome. The downstream sequences in pAeT3 are also homologous to the NADP-linked reductase gene region from the Zoogloea clone pUCDBK1. The sequences of the *Alcaligenes* thiolase and reductase genes is shown in FIG. 3.

Cloning of the individual thiolase and reductase genes from pAeT3 into pKK 223.3, leads to expression of the corresponding enzymes. Comparisons of the Zoogloea and *A. eutrophus* thiolase protein sequences establish that the two proteins are 63% homologous, including the active site Cys-89.

Both the *A. eutrophus* and Zoogloea thiolase gene regions were used as hybridization probes to screen Nocardia and *Pseudomonas olevorans* DNA for homologous genes. Techniques for identifying the thiolase, reductase, and other synthetase genes from other species having homologous sequences in addition to those described above, are known to those skilled in the art.

Identification of the *Z. ramigera* PHB polymerase gene

PHB polymerase from *Z. ramigera* utilizes D(−)-hydroxybutyryl-CoA monomers, polymerizing them in oxoester linkages in a template-independent head to tail condensation to yield linear polymers. These polymers can contain up to 10,000 monomer units with a molecular weight in excess of $1 \times 10^6$. The polymer rapidly becomes insoluble and accumulates as discrete granules in the cell.

As described in U.S. Ser. No. 067,695 filed Jun. 29, 1987, a conjugal transfer system based on derivatives of the broad host range plasmid pRK290, described by Ditta et al., in *Proc. Natl. Acad. Sci. USA* 77, 7347–7351 (1980), transposon mutagenesis and complementation analysis can be used in conjunction with the isolation, characterization and complementation of PHB negative mutants to isolate the PHB polymerase gene for *Z. ramigera* and *A. eutrophus*. As described by Schlegel et al., *Arch. Microbiol.* 71, 283–294 (1970), sudan-black staining is used for the detection of PHB negative mutants. Complementation of the mutants is screened for by growing, harvesting, and lysing the cells to release PHB that can then be purified to determine its presence and molecular weight distribution. Thiolase, reductase and PHB polymerase activities in the lysates are also assayed.

Identification of the *A. eutrophus* PHB polymerase gene

These techniques were also applied to the cloning, sequencing and expression of the PHB polymerase gene (phbC) in *Alcaligenes eutrophus* H16 using complementation of poly($\beta$)-hydroxybutyrate-negative mutants of *A. eutrophus* H16. The results demonstrate that the genes encoding the three enzymes of the PHB biosynthetic pathway are organized phbC-phbA-phbB. Expression of all three genes in *E. coli* results in a significant level (50% dry cell weight) of PHB production in this bacteria. phbC encodes a polypeptide of $Mr = 63,900$ which has a hydropathy profile distinct from typical membrane proteins indicating that PHB biosynthesis probably does not involve a membrane complex.

The strategy of constructing, characterizing and complementing PHB-negative mutants of a derivative (11599 S1 , Table 1) of *A. eutrophus* H16 was used to identify and isolate the gene(s) encoding PHB polymerase. Transposon mutagenesis allowed use of DNA hybridization analysis to map the chromosomal location of the Tn5 insertion in any interesting strains. 32 potential PHB negative mutants were identified by their opaque colony phenotype when grown on nitrogen limited minimal agar plates. Due to the procedure used to enrich for PHB-deficient strains, it was not surprising that the 32 mutants were found by DNA hybridization using a Tn5 DNA probe to belong to only three classes. More detailed DNA hybridization studies were then used to analyze a representative from each class, i.e., strains PHB #2, PHB #3 and PHB #19. From these studies, it was possible to conclude that in the case of strain PHB #2 and strain PHB #3, the Tn5 insertion causing the opaque phenotype was located in the chromosome approximately 1.2 kb and 1.6 kb, respectively, upstream from the phbA-phbB genes, as illustrated on FIG. 3. For strain PHB #19, the Tn5 insertion was located elsewhere on the *A. eutrophus* chromosome.

The experimental procedure and materials used in the isolation and characterization of phbC were as follows. The procedures and materials are similar to those described for isolation of the phbA and phbB genes.

Bacterial strains and plasmids are shown in Table 1. Media and culture conditions are as decribed above.

TABLE 1

| Bacterial Strains and Plasmids. | | |
|---|---|---|
| Strain | Relevant Characteristics | Reference |
| *E. coli* | | |

TABLE 1-continued

Bacterial Strains and Plasmids.

| Strain | Relevant Characteristics | Reference |
|---|---|---|
| JM83 DH5α | Host strain for plasmids | BRL |
| *A. eutrophus* | | |
| H16 | Wild type strain | ATCC17699 |
| 11599 | — | NCIB 11599 |
| 11599S1 | Strep$^r$ | |
| PHB#2 | H16[phb2::Tn5] | |
| PHB#3 | H16[phb3::Tn5] | |
| PHB#19 | H16[phb19::Tn5] | |
| Plasmids | | |
| pAeT29 | phbA-phbB | |
| pAeT10 | phbA-phbB | |
| pLAFR3 | Tc$^r$, cosmid vector | B. Staskawicz |
| pRK2013 | Nm$^r$ | |
| pRK602 | Cm$^r$, Nm$^r$, pRK2013 nm::Tn9 containing Tn5 | |
| pUC18 | Ap$^r$ | |
| pUC19 | Ap$^r$ | |

DNA manipulations were similar to those described above. Restriction endonucleases, T4 DNA ligase and DNA polymerase 1 were obtained from New England Biolabs and used as directed by the manufacturer. Calf intestinal alkaline phosphatase was purchased from Boehringer Mannheim Corporation. All routine DNA manipulations, including plasmid purifications, E. coli transformations, etc. were performed using methods described by Maniatis, et al. Chromosomal DNA was purified from *A. eutrophus* strains, grown to late logarithmic phase in TSB as described previously. Transfer of restriction digested DNA samples from agarose gels to nitrocellulose filters, prehybridization and hybridization with $^{32}$P-labelled DNA probes was as previously described. Rapid plasmid isolation from *A. eutrophus* recombinant strains, for restriction analysis, was performed by the alkaline extraction procedure.

Conjugation in *A. eutrophus*

The conjugal transfer of the broad host range plasmid, pLAFR3, or recombinant derivatives of pLAFR3, into *A. eutrophus* was performed using the same method as previously described. In this case, however, the recipient *A. eutrophus* cells were not sonicated and transconjugants were selected on *A. eutrophus* mineral agar plates containing 0.01% NH$_4$Cl as nitrogen source, 1% (w/v) fructose as carbon source and 10 µg/ml tetracycline.

For Tn5 mutagenesis, a spontaneous streptomycin resistant strain of *A. eutrophus* 11599 (1599 S1) was used. Transfer of pRK602 (Tn5) was carried out as described above using *E. coli* MM294A (pRK602) as the only donor. *A. eutrophus* strains containing Tn5 were selected for by growth on streptomycin (500 µg/ml) and kanamycin (100 µg/ml).

Amplification and Identification of PHB-Deficient Mutants

The amplification and screening procedures described by Schlegel and Oeding, *Radiation and Radioisotopes for Industrial Microorganisms*. International Atomic Energy Agency, Vienna, 223-231 (1971) was used to identify PHB-deficient strains of *A. eutrophus*. A pool of around $10^5$ Kan$^r$ transconjugants (Tn5 insertion mutants) was inoculated into 10 ml of mineral media containing 0.01% NH$_4$Cl, 1% fructose and 100 µg/ml kanamycin and incubated for 18 h at 30° C. This culture was then used to inoculate 100 ml of the same medium and incubated for 30 h at 30° C. To amplify PHB-deficient mutants, aliquots of this culture containing approximately $10^9$ cells were fractionated on sucrose step gradients by density equilibrium centrifugation and plated out on mineral agar plates containing 0.01% NH$_4$Cl, 1% fructose and 100 µg/ml kanamycin. After growth for 4–5 days at 30° C., opaque (PHB-deficient) and white (PHB-containing) colonies were readily distinguished. By quantitating the level of PHB produced by both opaque and white colonies, it was confirmed that opaque colonies were PHB-deficient whereas white colonies contained PHB.

Analysis of Proteins

In order to perform assays for β-ketothiolase, NADPH-linked acetoacetyl-CoA reductase and PHB-polymerase, 100 ml cultures of *A. eutrophus* strains were grown at 30° C. for 40 hours in TSB. For Tn5 mutant strains, kanamycin was added at 100 µg/ml and for strains containing pLAFR3 or derivatives thereof, tetracycline was added to 10 µg/ml. Cells were harvested by centrifugation, resuspended in 2 ml lysis buffer (10 mM Tris HCl, pH 8.0; 5 mM β-mercaptoethanol; 5 mM EDTA, 0.02 mM phenyl-methyl-sulfonyl-fluoride; 10% v/v glycerol) and lysed by sonication. An aliquot of the lysate was cleared of cell debris by centrifugation for β-ketothiolase and acetoacetyl-CoA reductase assays. β-ketothiolase activity was determined by measuring the rate of thiolysis of acetoacetyl-CoA as described by Davis, et al., *J. Biol. Chem.* 262,82–89 (1987), of acetoacetyl-CoA with NADPH as the cofactor. PHB polymerase assays were performed using samples of the crude lysate and determining the level of incorporation of D-$^3$H-hydroxybutyryl-CoA (specific activity approximately 2 µCi/µmol), as described by Fukui, et al., *Arch. Microbiol.* 110, 149–156 (1976). Protein concentrations were determined by the method of Bradford, *Anal. Biochem.* 72, 248–254 (1976), using Biorad assay solution and bovine serum albumin as the standard. *E. coli* maxi-cell labelling studies were performed as described by Sancar, et al., *J. Bacteriol.* 137, 692–693 (1979).

PHB Purification and Quantitation

To determine the level of PHB in different strains, 100 µl aliquots of the crude lysates were treated with 1.2 ml of 5% Na hypochlorite solution for 1 h at 37° C. The insoluble PHB was then harvested by centrifugation for 10 min in a microcentrifuge, washed successively with 1 ml of H$_2$O, 1 ml acetone, 1 ml of ethanol and dried under vacuum. PHB concentrations were then determined spectrophotometrically as described by Law and Slepecky, *J. Bacteriol.* 82, 33–36 (1961) using a standard curve and expressed as mg PHB/mg protein.

Plasmid Constructions and Complementation Analysis

Plasmids pLA29, pLA40, pLA41 and pLA42 were constructed by cloning restriction fragments of the pAeT29 insert into the broad host range vector pLAFR3 for complementation analysis of the PHB-negative *A. eutrophus* strains. pLAFR3 is a derivative of pLAFR1, described by Friedman, et al., *Gene* 18, 289–296 (1982), containing a pUC8 polylinker cloning site inserted into the EcoR1 site. Different fragments of pAeT9 were cloned into pLAFR3. pLA29 was constructed by ligating the entire 15 kb EcoR1 insert from pAeT29 into the EcoR1 site of pLAFR3. To facilitate the construction of pLA40, pLA41 and pLA42, the corresponding fragments were first cloned into pUC18 to produce plasmids pAeT40, pAeT41 and pAeT42. The fragments were then excised by digestion with BamHI and EcoR1 from the pUC18 plasmids, purified following agarose gel electrophoresis and ligated into BamH1/HindIII digested pLAFR3. To construct pAeT40, pAeT29 DNA was digested to completion with Nde1 and the cohesive ends filled in using the Klenow fragment of DNA polymerase. After separating the fragments on an agarose gel, the 7 kb fragment of interest was purified by electroelution, ligated into the Sma1 site of pUC18 and the recombinant plasmid pAeT40 subsequently identified by restriction analysis after transforming E. coli DH5αcells. This construction eliminates the acetoacetyl-CoA reductase activity since one of the Nde1 sites is located within the structural gene for this enzyme. For the construction of pAeT41, Sma1/EcoR1 digested pAeT29 DNA was separated on an agarose gel and the 5 kb Sma1/EcoR1 fragment purified and ligated into Sma1/EcoR1 digested pUC18 to give the correct plasmid. Deletion of the 2.3 kb Pst1 fragment containing the $\beta$-ketothiolase and acetoacetyl-CoA reductase structural genes by partial Pst1 digestion of pAeT41 DNA and religation was used to construct pAeT42.

Hybridization Mapping of Tn5 Insertions

A library of $10^5$ individual Tn5 insertion mutants of A. eutrophus 11599 S1 was constructed and 32 potentially PHB-negative colonies, identified by their opaque colony phenotype on nitrogen limited minimal plates, as described above. These were further characterized using Southern DNA hybridization analysis. For the DNA hybridization studies restriction digested chromosomal DNA from each strain was analyzed using both a Tn5 DNA probe (plasmid pRK602) and two plasmids, pAeT10 and pAeT29 which contain the A. eutrophus phbA-phbB locus (FIG. 3).

The 32 "opaque" strains represented multiple copies of only three distinct mutant types. These three distinct mutant types are represented by strains PHB #2, PHB #3 and PHB #19. For strains PHB #2 and PHB #3, the transposon Tn5 is inserted into chromosomal Pst1 fragments of 2.3 kb and 0.6 kb, respectively. Both of these chromosomal Pst1 fragments are located on the 15 kb of A. eutrophus DNA cloned in plasmid pAeT29, but not in the phbA-phbB structural genes. Strain PHB #19 has Tn5 inserted into a Pst1 fragment, not present on the pAeT29 plasmid.

More detailed DNA hybridization experiments were performed on the chromosomal DNA from strain PHB #2 and strain PHB #3 to map the site of the Tn5 insertion in each of these mutants. Chromosomal DNA from each of these strains as well as the wild type strain H16 and strain PHB #19 was digested with Sal1, Sma1 and Bgl1III, transferred bidirectionally to nitrocellulose filters and hybridized with Tn5 DNA (pRK602) and pAeT29 DNA probes to map the location of the Tn5 insertions in strains PHB #2 and PHB #3.

The results of a biochemical analysis of wild type H16 and each of the mutuant strains PHB #2, PHB #3, and PHB #19 is presented in Table 2. 100 ml stationary phase cultures of each strain were harvested, lysed and assayed for PHB content and $\beta$-ketothiolase, NADP-specific acetoacetyl-CoA reductase and PHB polymerase activities. Under these growth conditions wild type H16 produces a significant level of PHB (1.3 mg PHB/mg protein, Table 2) and has a high level of all three enzyme activities. Mutant strains PHB #2 and PHB #3 produce essentially no PHB and strain PHB #19 produces only 50% of the wild type level (Table 2). PHB polymerase activity could not be detected in any of these mutant strains, however, the presence of PHB in the lysate of strain PHB #19 indicates that the enzyme is there although the activity is probably below the detection level of the assay. $\beta$-ketothiolase activities in all three mutants are reduced to the order of 45% (PHB #2) to 38% (PHB #19) that of wild type strain H16. Similarly, NADP-specific acetoacetyl-CoA reductase activities are around 50% of the wild type level. It was concluded from these data that the PHB-polymerase gene was located upstream from phbA-phbB and that the expression of the latter genes is affected by the Tn5 insertion upstream in the case of strains PHB #2 and PHB #3.

A series of plasmids containing fragments of the A. eutrophus insert of plasmid pAeT29 were constructed in the broad host range vector pLAFR3 for complementation analysis of the PHB-negative mutants.

Each of the recombinant plasmids, pLA29, pLA40, pLA41 and pLA42 were introduced into each of the A. eutrophus strains by conjugation and the resulting transconjugants analyzed on nitrogen limited plates for the restoration of the white (PHB plus) phenotype. Plasmids pLA29, pLA40, pLA41 and pLA42, each of which contains the region upstream from phbA-phbB into which Tn5 has inserted in the chromosome of strains PHB #2 and PHB #3, complemented the mutation in each of these two strains, restoring the white colony phenotype. All four recombinant plasmids also restored the wild type colony phenotype to mutant strain PHB #19. In the case of this strain, the Tn5 insertion is located outside the region of the A. eutrophus chromosome contained in each of the plasmids. Control experiments using the vector pLAFR3 resulted in the opaque colony phenotype when introduced into each of the three mutant strains.

Biochemical analysis of each of the complemented strains was performed as described for the characterization of the mutants and these results are also presented in Table 2. The introduction of pLA29 into each of the mutant strains results in the restoration of PHB polymerase activity and PHB biosynthesis (Table 2). In addition, an approximately three to five-fold increase in the levels of $\beta$-ketothiolase and NADP-specific acetoacetyl-CoA reductase activities was observed. Plasmid pLA40 and pLA41 also restore PHB-polymerase and PHB production to strains PHB #2 (Table 2), PHB #3 and PHB #19, although in the case of pLA40, the phbB gene was disrupted during the construction of this plasmid. Finally, plasmid pLA42 restores PHB polymerase activity and PHB production to all three mutant strains although the phbA-phbB genes have been deleted. In the case of strains containing this plasmid the $\beta$-ketothiolase and NADP-specific acetoacetyl-CoA reductase activities remain at the same level as the mutant strains (Table 2).

TABLE 2

Biochemical analysis of mutant and complemented A. eutrophus H16 strains.

| Strain | PHB[1] | Thio-lase[2] | Reduc-tase[2] | Polymer-ase[3] ($\times 10^3$) |
|---|---|---|---|---|
| H16 | 1.3 | 8.9 | 1.0 | 3.9 |
| PHB#2 | <0.01 | 4.0 | 0.5 | ND |
| PHB#3 | <0.01 | 3.4 | 0.5 | ND |
| Tn5#19 | 0.6 | 3.2 | 0.4 | ND |
| H16/pLA29 | 1.0 | 28.7 | 9.2 | 5.3 |
| PHB#2/pLA29 | 1.5 | 27.5 | 3.5 | 3.8 |
| PHB#3/pLA29 | 0.9 | 24.8 | 4.4 | 0.7 |
| PHB#19/pLA29 | 1.8 | 26.7 | 4.9 | 1.0 |
| PHB#2/pLA40 | 0.9 | 20.4 | 0.45 | 0.6 |
| PHB#2/pLA41 | | 18.0 | 3.7 | 0.9 |
| PHB#2/pLA42 | 1.2 | 2.0 | 0.3 | 4.3 |
| PHB#3/pLA42 | 0.9 | 5.5 | 0.5 | 0.6 |
| PHB#19/pLA42 | 1.2 | 5.5 | 0.4 | 0.6 |

[1]mg/mg of protein
[2]units/mg of protein
[3]cpm/min/mg of protein
ND: no detectable activity
Results shown are the average of two or more experiments.

As described above, the phbA-phbB genes located on plasmid pAeT29 were expressed in E. coli under the control of the A. eutrophus promoter. Identification of the phbC gene upstream from phbA-phbB together with the observed decrease in thiolase and reductase enzyme activities in strains PHB #2 and PHB #3 indicates that all three genes are expressed from a single promoter located upstream from phbC. To study this, cultures of E. coli strains containing plasmids pAeT41 and pAeT42 were grown under nitrogen limiting conditions until cells reached stationary phase at which point the cells were harvested, lysed and analyzed. E. coli containing pUC18 was used as a control. The results of β-ketothiolase, acetoacetyl-CoA reductase, PHB polymerase and PHB concentration assays, shown in Table 3, indicate that the lysate of E. coli containing plasmid pAeT41 has a significant level of each enzyme activity and PHB production.

Maxi-cell analysis of the E. coli strains described above was used to determine the molecular weight of the polypeptides encoded by plasmids pAeT41 and pAeT42. Plasmid pAeT10 was included in the analysis as this plasmid expresses the A. eutrophus phbA-phbB genes from the pUC8 vector lacZ promoter. Additional protein bands are present of Mr 40,000 and Mr 26,000 in samples containing plasmid pAeT10 and pAeT41, respectively. Both of these plasmids express the phbA-phbB genes encoding β-ketothiolase (Mr 41,000) and NADP-specific acetoacetyl-CoA reductase (Mr 26,000). Neither of these two proteins is present in the extract of cells containing plasmid pAeT42 which does not contain the phbA-phbB genes. Control experiments in which the vector pUC8 was used gave no signal at Mr 41,000 or Mr 26,000. Both plasmids, pAeT41 and pAeT42, express the PHB polymerase (phbC) gene in E. coli, and in samples which contain extracts of cells containing these plasmids a signal at $M_r$ 58,000 is clearly evident. Again, this protein is absent from sample which contains the extract from cells containing plasmid pAeT10 which does not contain the phbC gene and also from a control sample of pUC8 containing cells. An additional band of around Mr 30,000 is present in all samples and was also found in control experiments of cell extracts containing pUC8 and is presumably a vector protein. From these data we conclude that the phbC gene expressed in E. coli encodes a polypeptide of approximately $M_r$ 58,000.

TABLE 3

Biochemical analysis of recombinant E. coli strains to determine expression of phbC-A-B in E. coli.

| Plasmid | Thiolase U/mg Protein | Reductase U/mg Protein | Polymerase cpm/min/mg Protein | PHB mg/mg Protein |
|---|---|---|---|---|
| pUC18 | 0.5 | ND | ND | 0.015 |
| pAeT41 | 59.0 | 2.5 | $2.4 \times 10^4$ | 2.977 |
| pAeT42 | 0.9 | ND | $0.02 \times 10^4$ | 0.011 |

ND: no detectable activity
Results shown are the average of two or more experiments.

Nucleotide Sequene Analysis of phbC

The 2 kb Sma1-Pst1 A. eutrophus Chromosomal DNA fragment cloned in plasmid pAeT42 contains the entire structural gene for phbC and probably the regulatory sequences. This fragment was sequenced from both DNA strands multiple times using the dideoxy sequencing method as described above. A single long open reading frame extends from nucleotide 820 to a TGA stop codon at nucleotide 2608. Potential translation initiation codons are present at position 842 (ATG), 1067 (ATG) and 1097 (ATG). Translation from each of these potential start sites would produce proteins of Mr 63,940, Mr 55,513 and Mr 54,483, respectively. Significant amino acid sequence homology between the translation product from the ATG at position 842 to the ATG at position 1067 and the P. oleovorans PHA polymerase gene product, described below, indicates that the first ATG (position 842) is probably correct. FIG. 4 presents the entire nucleotide sequence of this region from the Sma1 site to the first 30 nucleotides of the phbA gene located downstream. The translation product of the open reading frame from the ATG at position 842 to the TGA at position 2609 is also shown. The PHB polymerase encoded by the phbC gene in plasmid pAeT42 is a polypeptide of 589 amino acids with an Mr=63,940. The N-terminal 10 amino acids of the phbA gene product are also presented in FIG. 4. Additional features of the nucleotide sequence presented in FIG. 4 include the C-terminus of an open reading frame which begins upstream from the Sma1 site and terminates at the TGA stop codon at position 76. Located 85 bp downstream from the phbC TGA stop codon (position 2609) lies the ATG start codon for the phbA structural gene (position 2969). From these data it is clear that the three enzymes of the A. eutrophus PHB biosynthetic pathway are encoded by three genes organized as phbC-phbA-phbB as illustrated in FIG. 4.

The expression of phbC alone in E. coli produces neither PHB nor significant levels of PHB polymerase activity (plasmid pAeT42). E. coli appears incapable of synthesizing D-(—)-hydroxybutyryl-CoA, as substrate for PHB polymerase, in the absence of the A. eutrophus phbA-phbB genes. Since the insert of pAeT42 contains both the promoter and structural gene for phbC (plasmid pLA42 complements all PHB-negative mutants, Table 2), it can be concluded that in the absence of available substrate, PHB polymerase is inactive or degraded in E. coli.

The nucleotide sequence of the A. eutrophus chromosomal DNA insert in plasmid pLA42 encoding PHB polymerase predicts a single polypeptide of Mr 63,940 (FIG. 4). Although PHB polymerase has not previously been purified and characterized, the results of E. coli maxi-cell studies indicate a $M_r=58,000$ for this polypeptide, in reasonable agreement with that predicted from the gene sequence.

For a number of years, it was proposed that the polymerization of (D)-β-hydroxybutyryl-CoA involves a membrane bound polymerase which forms a type of barrier between the aqueous environment of the cytoplasm and the hydrophobic crystalline PHB granules. The hydropathy profile of the PHB polymerase polypeptide does not indicate a typical membrane spanning structure. In addition, NMR studies of native PHB granules in Methylobacterius indicate that these granules are in a mobile, as opposed to a highly crystalline solid state. Together these data lend credence to the idea that PHB biosynthesis does not in fact require a complex membrane bound polymerization system. The mechanism for PHB polymerase proposed in the literature involves two partial reactions. The initial acyl-S-enzyme intermediate formation is followed by transfer to a primer acceptor in the second reaction. The predicted primary structure of PHB polymerase has 5 cysteine residues, $Cys_{246}$, $Cys_{319}$, $Cys_{382}$, $Cys_{438}$ and $Cys_{459}$.

Identification of the P. oleovarans PHA Polymerase gene

The genes involved in the biosynthesis of polyhydroxyalkanoate (PHA) polyesters in *Pseudomonas oleovorans* were also isolated, as follows.

In 1983, de Smet, et al. *J. Bacteriol.* 154,870–878, identified a polymer produced by *Pseudomonas oleovorans* TF4-1L (ATCC 29347) as poly-B-hydroxyoctanoate. Subsequent studies showed that P. oleovorans could produce a range of PHA biopolymers depending on the carbon source used, i.e., n-alkanes and 1-alkenes (Lageveen, et al., *Appl. Environ. Microbiol.* 54,2924–2932 (1988)) or fatty acids (Brandl, et al., *App. Environ. Microbiol.* 54,1977–1982 (1988). The pathway appears to involve the conversion of the alkanes/alkenes to the fatty acid which then enters the fatty acid B-oxidation pathway, resulting in the formation of the D isomer of the B-hydroxyacyl-CoA, which is incorporated into the polymer by PHA polymerase. P. oleovorans has not been shown to incorporate B-hydroxybutyrate indicating that 1) it does not possess the thiolase/reductase enzymes, or 2) the PHA polymerase cannot use B-hydroxybutyrate as a substrate. The broad range of substrates used by the P. oleovorans PHA polymerase make the gene encoding this enzyme particularly interesting for biopolymer engineering of polyesters.

Figure 6:
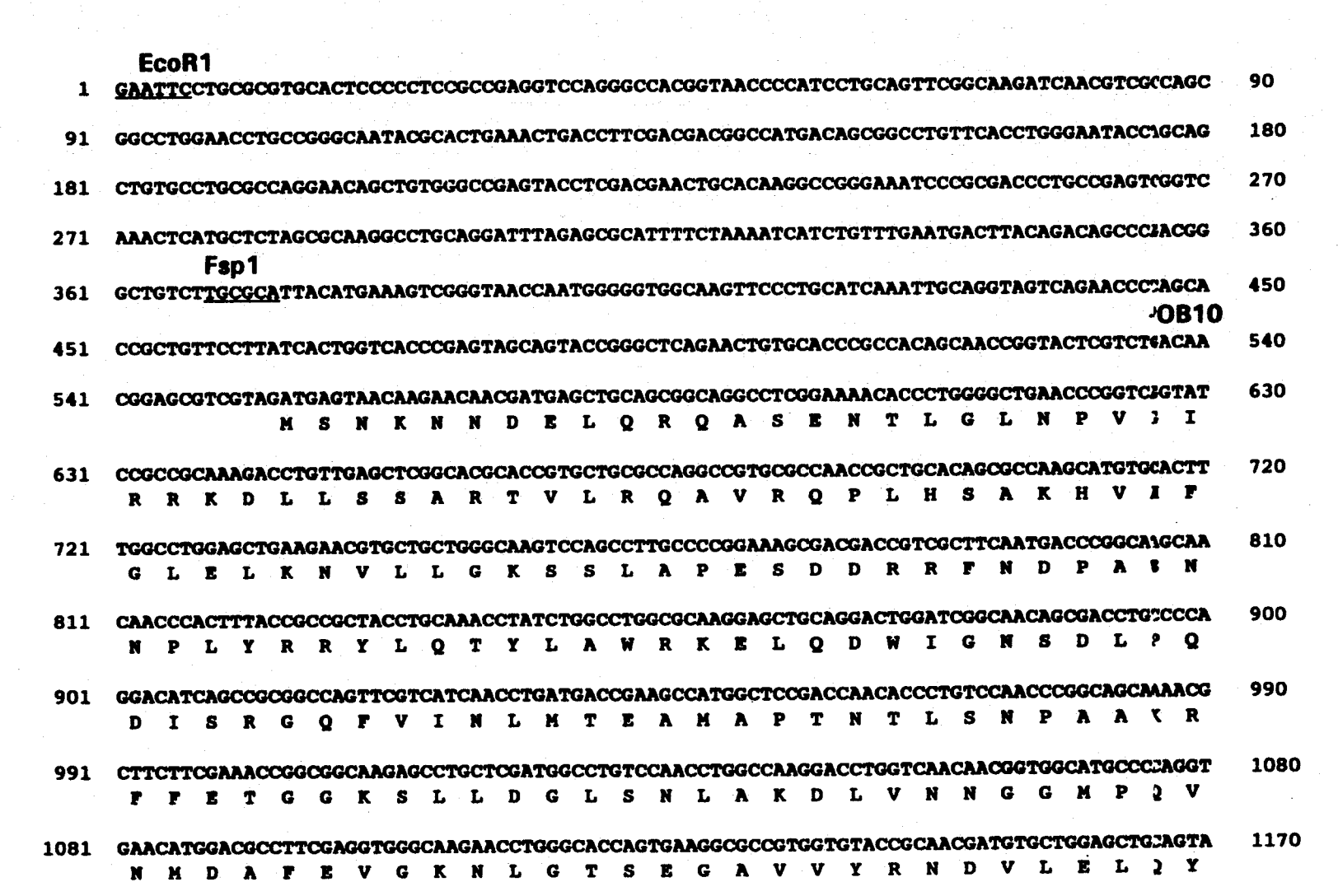

The approach used for isolating the A. eutrophus B-ketothiolase and NADP-specific acetoacetyl-CoA reductase using the Z. ramigera B-ketothiolase gene as a DNA hybridization probe was followed, as described above, to isolate the P. oleovorans PHA polymerase gene. Southern DNA hybridization of P. oleovorans chromosomal DNA identified a 6 kb EcoR1 restriction fragment with strong homology to the A. eutrophus PHB polymerase gene (phbC). The 6 kb EcoR1 fragment was cloned in the E. coli plasmid vector, pUC18, by standard procedures to give plasmid pP023. The region which hybridized to the A. eutrophus phbC gene is located as indicated on FIG. 5. Nucleotide sequence analysis of the complete 6 kb fragment identified three potential protein coding regions (open reading frames, ORF1, ORF2 and ORF3, indicated on FIG. 5). ORF1 begins at the ATG initiation codon nucleotide 554 and ends at the TGA stop codon nucleotide 2231 (FIG. 6). This open reading frame is contained in the region of the pP023 insert which hybridizes with the A. eutrophus phbC gene. ORF1 encodes a polypeptide of 562 amino acids with an $M_r=60,000$. A comparison of the protein sequence predicted by translation of ORF1 with the amino acid sequence of the A. eutrophus PHB polymerase using the program ALIGN revealed 52% identity between the two proteins. These data identify ORF1 as the P. oleovorans PHA polymerase gene. ORF2 begins at the ATG position 2297 and ends at the TAA position 3146. ORF3 begins at the ATG position 3217 and ends at the TGA position 4948. ORF2 and ORF3 are probably cotranscribed with the PHA polymerase gene (ORF1) and are probably proteins involved in PHA biosynthesis.

Synthesis of PHB, PHA and similar polymers

It was established above that it is possible to construct new PHB production strains by introducing the A. eutrophus PHB biosynthetic genes into E. coli resulting in the accumulation of up to 50% dry cell weight as PHB. The construction of new or improved polyester production strains is now possible by the expression of either the PHB biosynthetic genes from A. eutrophus or the PHA polymerase gene and ORF2 and ORF3 from P. oleovorans in a number of systems. Plasmids can be constructed which express the A. eutrophus B-ketothiolase and NADP-specific acetoacetyl-CoA reductase genes in P. oleovorans under the control of the xylS promoter in the broad host range expression plasmids pNM185 (Mermod, et al. *J.Bacteriol.* 167, 447–454 (1986), or pERD20/pERD21 (Ramos, et al, *FEBS LETTERS* 226, 241–246 (1986). Alternatively, the broad host range tac promoter expression vectors pMMB24/pMMB22 (Bagdasarian, et al, *Gene* 26, 273–282 (1983)). These same vectors can also be used to express the A. eutrophus PHB polymerase gene or the three P. oleovarans genes cloned in plasmid pP023 (FIG. 5).

Two plasmids, pLAP1 and pLAP2, have been constructed which should express the P. oleovorans PHA polymerase gene and ORF2 (pLAP1) or the PHA polymerase gene and ORF2 plus ORF3 (pLAP2) under the control of the A. eutrophus phbC promoter (FIG. 4).

To construct these plasmids, the 810 bp Sma 1-BstB 1 restriction fragment spanning the first 810 nucleotides of the A. eutrophus insert in plasmid pAeT42 containing the phbC promoter was ligated into the unique Sma 1 site in the E. coli vector pUC19 to obtain plasmid pAeTB1. The P. oleovorans PHA polymerase gene promoter was removed by using the exonuclease Bal31 to delete 170 bp from the end of Fsp1 digested pP023 DNA and recovering the PHA polymerase structural gene plus ORF2 by subsequently digesting with Cla1, and cloning the fragment into Sma1/Cla1 digested pBLSK+vector (Stratagene, La Jolla Calif. 92037). The insert of pPOB10 was identified as containing the last 19 bp upstream from the ATG start codon of the PHA polymerase structural gene (nucleotide 535, FIG. 62) the complete PHA polymerase structural gene and ORF2. The structural gene and ORF2 could then be recovered on a 2.6 kb BamH1- Xho1 fragment and ligated into BamH1/ Sal1 digested pAeTB1 to obtain plasmid pAeP1. The entire insert of pAeP1 containing the phbC promoter -PHA polymerase structural gene - ORF2 construct was then excised as a 3.4 EcoR1 - Hind111 fragment and cloned into the polylinker region of the broad host range vector pLAFR3 for conjugation into A. eutrophus strains. To construct pAeP2, the 2.6 kb BamH1 - Cla1 fragment from pPOB10 and the 2.5 kb Cla1 - Xho1 fragment from pPO23, containing ORF3(FIG. 66), were ligated with BamH1/Sal1 digested pAeTB1 to obtain pAeP2. Again the phbC - PHA polymerase - ORF2 - ORF3 construct could be excised as a 5.9 kb EcoR1- HindIII fragment and cloned into the polylinker region of pLAFR3 to obtain pLAP2. pLAP1 should express both the PHA polymerase and ORF2 in *A. eutrophus* and pLAP2 should in addition express ORF3. If the genes are not expressed, they can be inserted into the broad host range expression vectors described above for the B-ketothiolase and NADP-specific acetoacetyl-CoA reductase genes.

The PHB polymerase and PHA polymerase genes should prove invaluable for the production of PHA polymers in bacterial and plant systems. However, the cloned and characterized genes can be further modified by constructing fusions of the two polymerases or by chemical mutagenesis. Functional polymerase enzymes could then be selected in an appropriate organism by the accumulation of polymer detectable by phenotypic appearance or increased density. This is a straightforward approach to altering the enzyme's specificity to create novel polymerases.

Modification of Polymer Synthesis by Varying Levels of Enzyme Expression

After isolation and characterization of the polymer genes and gene products from a variety of organisms, as demonstrated for *Z. ramigera, A. eutrophus, N. salmonicolor,* and *P. oleovorans,* a means for controlling the expression of the gene products can be established. Overproduction of the Zoogloea thiolase gene was demonstrated by the studies used to define the transcription start site and promoter of the *Z. ramigera*. Overproduction enables the purification of the enzymes to homogeneity and provides reagent type quantities for analysis and comparison of substrate specificieties. In addition, the purified enzymes can be used to synthesize stereospecific substrates for in vitro polymer synthesis. Further, once the transcriptional regulatory mechanism responsible for polymer overproduction is elucidated under a variety of environmental conditions, in vitro systems for the enzymatic synthesis of known polymers, and novel polymers, can be developed to provide new materials. The new materials are then analyzed for chemical composition, molecular weight and rheological characteristics so that maximum utilization can be made of the polymers.

An overproduction system for the *Z. ramigera* thiolase in *E. coli* was constructed using the synthetic tac promoter to produce a series of thiolase expression plasmids, the optimum construct in induced in *E. coli* cells yielding about 20-30% of the total soluble cell protein as thiolase. This method yields thiolase in reagent type quantities, an average of 150 mg of pure thiolase from 1 liter of culture.

There are essentially two conditions where gene regulation in *Z. ramigera* and *A. eutrophus* may be expected to occur: when carbon starved cells under nutrient limiting conditions are subsequently presented with a carbon source and when cells grown under nutrient limiting conditions have accumulated large amounts of PHB and the nutrient limitation is removed, resulting in PHB degradation.

Transcriptional regulation of the polymer biosynthetic genes is determined as follows. Cultures grown under various conditions are harvested both for enzyme assays (thiolase, reductase and synthetase) and for RNA purification. RNA samples are analyzed in a series of Northern hybridization experiments using the cloned genes as probes. Useful RNA hybridization methodology includes glyoxylation of RNA (McMaster and Carmichael, *Proc. Natl. Acad. Sci. USA* 74, 4835 (1977)); formaldehyde/agarose gel electrophoresis (Lehrach et al., *Proc. Natl. Acad. Sci. USA* 16, 4743 (1977)); transfer to nitrocellulose or nylon filters (Thomas, *Proc. Natl. Acad. Sci. USA* 77, 5201 (1980)); and hybridization with DNA probes labelled with $^{32}P$ by nick translation (Rigby et al., *J. Mol. Biol.* 113, 237 (1977)). DNA probes are prepared from clones pUCDBK1 (*Z. ramigera*); and pAeT3 (*A. eutrophus*). One result of these studies is the establishment of the operon organization of the genes and the length of the mRNA.

The levels of each of the biosynthetic enzymes are manipulated and the effect this has on polymer synthesis monitored. It is necessary to determine the rate-limiting enzyme(s) in the biosynthetic pathway so that one can increase flux through the pathway by overproducing the rate-limiting enzyme(s); the effect overproduction of each enzyme has on the incorporation of different monomeric units, i.e., the ratio of PHB:PHV in the copolymer produced by *A. eutrophus* when grown on butyrate; and the result of expression of the genes from one species in other species, for example, the expression of Zoogloea genes in *A. eutrophus*, and vice versa, as well as other isolated and characterized heterologous genes from other organisms, e.g., Nocardia and *P. oleovorans* in Zoogloea and *A. eutrophus*.

To accomplish overproduction of polymer biosynthetic genes in multiple host organisms, one must use broad host range expression vectors which function in these bacteria. In one instance, enzyme overproduction via gene dosage is carried out. For example, the entire pUCDBK1 insert containing the promoter region can be cloned into the vector pSUP104 (Simon et al., *Molecular Genetics of the Bacteria-Plant Interaction*, A. Pobler, ed. (Spring-Verlag, NY 1983) and used to transform *Z. ramigera* I-16-M. The extent of overproduction of each enzyme is monitored by enzyme assays. A similar approach can be taken for any number of other genes; for example, thiolase; thiolase and reductase; reductase; reductase and synthetase, etc. Secondly, genes can be placed under the transcriptional control of high efficiency promoters, i.e., tac (Gill et al., *J. Bact.* 167, 611-615 (1986) and tol (Mermod et al., *J. Bact.* 167, 447-454 (1986). In this case, the constructs are conjugated into mutants defective in the corresponding gene. The expression of the polymer biosynthetic gene or genes of interest can then be tightly regulated, as determined using enzyme assays to monitor the level of overproduction. As each construct is tested, one can begin to monitor the effect on polymer synthesis in a routine manner i.e., the rate and level of synthesis.

Modification of Polymer Synthesis by Altering Available Substrate or Enzyme Specificity Factors which determine the molecular weight of the PHB or PHA produced by different bacteria can be eludicated by analysing the molecular weight distribution of the polymers produced by various bacteria. There is little doubt that a number of PHB-producing microorganisms have the ability to incorporate monomers other than D(—)-hydroxybutyrate into the polymer chain. For the PHB-PHV copolymer produced by *A. eutrophus*, it has been proposed that propionate is first converted to propionyl-CoA which then acts as a substrate for beta-ketothiolase. The high yields of pure enzymes available from overproduction systems is necessary to determine the range of alternate substrates which each of the three PHB-biosynthetic enzymes can utilize and the types of new PHB-like polymers that can be synthesized in an in vitro system where the available substrates can be strictly controlled.

Although the thiolase and reductase enzymes are an essential part of the biosynthesis of PHB and PHB-like polymers, it is the PHB polymerase which ultimately defines the new types of polymer which can be made. This is facilitated by the development of an in vitro system using the enzyme to test a whole range of substrates, many of which cannot enter the cell and therefore cannot be tested for incorporation into PHB by a fermentation process.

Overproduction and purification of more than one reductase enzyme provides a means for comparing the kinetics and specificity of the enzymes. The Zoogloea reductase has been reported to be NADP-specific, however, the A. eutrophus enzyme apparently will use either NAD or NADP. The stereospecificity of this enzyme may make it a useful reagent for the synthesis of D-substrates for PHB polymerase studies. Among the acetoacetyl derivatives to be tested are the oxoester of CoA and oxopantetheine pivaloate (OPP) and the methylene analogs. The ketone but not the oxoester of the methylene analogs is cleaved by Zoologea thiolase.

Various longer chain alkyl derivatives, in particular the $C_5$-$C_8$ linear 3-oxo thiolesters, oxoesters and methylene ketones, may also be useful as substrates for the PHB polymerase, given the existence of $C_5$-$C_8$-beta-hydroxyalkanoates in B. megaterium, as well as olefins, alcohols and epoxides.

In crude extracts of Z. ramigera, D-beta-hydroxybutyryl CoA, but not L-hydroxybutyryl CoA, is a substrate for PHB polymerase. It is expected that other D-hydroxyacyl CoA species can utilize alternate substrates or cosubstrates such as D-beta-hydroxyvaleryl CoA (HV-CoA). [2-$^3$H]HB-CoA and beta[3-$^{14}$C]-HV-CoA, each readily preparable by enzymic or chemical synthesis, can be used as substrates and to monitor $^3$H and $^{14}$C content and ratios in polymers precipitated or separated by gel filtration. It is predicted that block copolymer regions, e.g., $(HB)_{500}(HV)_{1000}(HB)_{500}$, can be constructed by careful control of substrate ratios, and leaving groups in elongation phase, e.g., HB-oxo-CoA and HV-S-CoA monomers.

Additional alternate substrates can be tested including branched chain beta-hydroxyacyl CoAs. Testing cannot be done in whole cells since such compounds are not normally transporte into the cells. Alternate substrates can be tested for inhibition of normal [$^{14}$C]-PHB formation first by incorporation of soluble [$^{14}$C]-HBCoA into insoluble polymer, then as copolymerization cosubstrates and finally for homopolymerization. Alternate substrates can be assayed for $K_m$, $V_{max}$ relative to HB-CoA and for polymer size determined by calibrated gel filtration studies.

Method for Production of PHB on a continuous basis

PHB is produced and stored in bacteria when they are grown under nutrient limiting conditions, usually nitrogen-limiting conditions (for example, 0.1% nitrogen, depending on the species), although culturing the bacteria under conditions providing limited oxygen, phosphate, or other non-carbon nutrient source will also induce PHB synthesis and storage. For example, Azotobacter beijerinckii, a nitrogen fixing bacteria accumulates up to 70% dry cell weight as PHB when grown on glucose/ammonium salts under limiting oxygen. Increasing the available oxygen leads to a decrease in PHB synthesis and a concomittant reduction in the levels of two of the biosynthetic enzymes. The reduction in enzyme levels is indicative of a regulatory mechanism(s) operating at the genetic level. Nitrogen limitation of the growth of Alcaligenes eutrophus results in yields of up to 80% dry cell weight PHB. Similarly, Halobacterium and Pseudomonas sp. increase PHB production under nitrogen limitation.

Under non-limiting conditions, the PHB in organisms that normally produce the PHB is rapidly degraded by degradative enzymes. It is possible to mutate these organisms such that the degradative enzymes are inactive or deleted, hence PHB accumulated during limiting conditions of growth cannot be degraded under non-limiting conditions. In order for these bacteria to resume growth, the PHB will be excreted into the medium. Alternatively, it is possible to introduce the requisite enzymes into an organism which does not metabolize PHB (biosynthesis or degradation), enabling that organism to accumulate large quantities of PHB under limiting conditions, and when conditions are changed to non-limiting, the organism should release the PHB into the medium.

By cycling the limiting and non-limiting conditions, it is possible to accumulate the maximum amount of PHB (based on absorbance of the bacteria, which increases as a function of polymer content), then release the accumulated polymer into the medium by changing the conditions to non-limiting conditions which stimulate replication of the bacteria. The organisms can be cultured in conventional fermentation systems for continuous removal of the polymer containing medium without disruption of the bacteria.

Expression in plants and production of PHB and PHA Polymers

As described above with reference to bacterial expression systems, the genes encoding the thiolase, reductase, and/or the polymerase for PHB or PHA can be expressed in plants of a variety of species to produce the desired polymeric product. The advantages of such a system are immediately apparent, decreasing dependence on petroleum-based plastics, and creating an economically useful crop for plants which can grow on a variety of soils.

The first requirement for plant genetic engineering is a system to deliver the foreign DNA to plant tissue. The most popular vectors at this time are the tumour-inducing (Ti) plasmids of Agrobacterium tumefaciens, using this bacterium as the agent to deliver DNA by infection. Plant DNA viruses can also be used as vectors, such as vectors based upon the cauliflower mosaic viruses or the Gemini virus vectors. There are also a number of methods of direct gene transfer to plant cells, including chemically stimulated DNA uptake by protoplasts, electroporation, electroinjection of intact plant cells, liposome-mediated transformation of protoplasts, and DNA transformation by direct injection into plants. Chemically stimulated uptake involves incubating protoplasts with donor and carrier DNA in the presence of 13% (w/v) polyethylene glycol in 40 mM $CaCl_2$. Post-incubation is carried out whereby the PEG concentrationis gradually lowered as the $CaCl_2$ concentration is gradually raised. Electroporation is the process whereby electrical pulses of high field strength are used to reversibly permeabilize cell membranes to facilitate uptake of large molecules, including DNA. Electroinjection and direct injection have the advantage that they do not require formation of protoplasts first. These methods are known to those skilled in the art. See, for example, the review by C. P. Lichtenstein and S. L. Fuller, "Vectors for the genetic engineering of plants", *Genetic Engineering*, ed. P. W. J. Rigby, vol. 6, 104–171 (Academic Press Ltd. 1987).

The genes can be introduced into the cytoplasm, mitochondria, or chloroplast, either directly or using targeting sequences. Vectors and targeting sequences and promoters for plants are known to those skilled in the art and are commercially available from Pharmacia-LKB Biotechnology, 800 Centennial Ave., Piscataway, N.J. 08854-9932, and Stragene, La Jolla, Calif.

Any type of plant which produces a useful carbon substrate can be engineered for polymer production. As used with reference to production of polymers in plants, "polymer" includes PHB, PHA, and novel carbon-based polymers synthesized from fatty acids using the disclosed polymerases. If the plant does not form the appropriate fatty acids, the thiolase and reductase genes can be introduced into the plant along with one or more polymerases. The *A. eutrophus* polymerase polymerizes C4 and C5 substrates. The *P. oleovarans* polymerase acts on longer substrates, such as C6 to C18 fatty acids, but not short chain fatty acids. The plants can also be modified, preferably by mutagenesis, to block the glycerol ester and fatty acid degradation pathways so that the plant forms the appropriate substrate.

The genes can be introduced into any type of plant. Cereal plants are preferred, such as corn, wheat and rice, since they are widely grown and their genetic systems are well characterized. Other useful agronomic plants include tobacco and high oil seed plants, especially those varieties which grow in desert or in mineralized soil.

The genes can also be introduced into plant cell culture systems, many of which are known to those skilled in the art. Cell culture of a variety of cereal and other agricultural crops is described in detail in *Handbook of Plant Cell Culture* vol. 4 edited by D. A. Evans, W. R. Sharp, and P. V. Ammirato (Macmillan Publishing Co. N.Y. 1986). A specific example of a plant system in which much genetic work has been conducted is *Arabidopsis thaliana*. Polymer production in cell culture can be manipulated not only by introduction of the cloned genes but also be variation in substrates and culture conditions, as described with reference to production in bacteria.

Modifications and variations of the present invention, a method for making polyhydroxybutyrate and polyhydroxybutyrate-like polymers having carbon-carbon backbones using recombinant engineering according to the foregoing detailed description, and the resulting polymers, will be obvious to those skilled in the art. Such variations and modifications are intended to come within the scope of the appended claims.

We claim.

1. An isolated DNA sequence encoding an enzyme hybridizing to a gene encoding polyhydroxybutyrate polymerase from *Alcaligenes eutrophus* or polyhydroxyalkanoate polymerase from *Pseudomonas oleovorans* when incubated for a period of approximately 16 to 18 hours at a temperature of 65° C. in a mixture of a 5× solution of 0.15 M NaCl, 0.15 M sodium citrate, 20 Mm sodium phosphate, 5× Denhardt's solution, 0.1% (w/v) SDS, 10 mM EDTA, and 100 μg/ml sonicated denatured salmon DNA.

2. The sequence of claim 1 encoding an enzyme expressed in a bacteria selected from the group consisting of Zoogloea, Alcaligenes, Bacillus, Nocardia, Clostridium, Halobacterium, and Pseudomonas.

* * * * *